United States Patent [19]

Shen et al.

[11] Patent Number: 5,295,830

[45] Date of Patent: Mar. 22, 1994

[54] ASEPTIC DENTAL VALVES AND INSTRUMENTS

[76] Inventors: James Shen, 18751 Beach Blvd., Huntington Beach, Calif. 92648; Rily Young, 8681 Luss Dr., Huntington Beach, Calif. 92646

[21] Appl. No.: 982,413

[22] Filed: Nov. 27, 1992

Related U.S. Application Data

[63] Continuation of Ser. No. 592,360, Oct. 3, 1990, abandoned.

[51] Int. Cl.$^5$ .......................... A61C 1/16; A61C 17/06; A61C 17/14
[52] U.S. Cl. .......................................... 433/116; 433/91
[58] Field of Search .................. 433/116, 91, 95, 96, 433/27; 604/32, 35, 247, 248, 902, 119, 268

[56] References Cited

U.S. PATENT DOCUMENTS

| | | | |
|---|---|---|---|
| 2,392,045 | 1/1946 | Hudgins | 604/247 |
| 2,485,900 | 10/1949 | McKeen | 433/116 |
| 2,531,730 | 11/1950 | Henderson | 604/902 X |

(List continued on next page.)

FOREIGN PATENT DOCUMENTS

| | | | |
|---|---|---|---|
| 463542 | 7/1928 | Fed. Rep. of Germany | 433/116 |
| 1002502 | 2/1957 | Fed. Rep. of Germany | 433/116 |

OTHER PUBLICATIONS

Contemporary Ob/Gyn, 1990, pp. 121-122: J. E. Gottesman, "Adding Protection During Endoscopic Procedures".

*Primary Examiner*—Gene Mancene
*Assistant Examiner*—Nicholas D. Lucchesi
*Attorney, Agent, or Firm*—D. Pressman

[57] ABSTRACT

Aseptic dental valves and instruments and accoutrements therefor comprise a handle extension (20—FIG. 2) and a flange guard (22) to be added within the path of a saliva ejector (FIG. 1) for preventing a dental professional's (DP's) hand from touching and contaminating the hose (14) or the hose valve (24), thereby to prevent microorganisms on the hand from contaminating these latter components where they might be picked up by the hand later and cross-contaminate subsequent patients. The handle extension and flange guard are useable on saliva ejectors (FIG. 3), surgical suction tips (FIG. 4), drills (FIGS. 12-12C), and air-water valves (FIGS. 14-15). The surgical tip can be formed of a series of sections of decreasing diameters in a stepped-down formation (FIG. 4A) to enable it to retain its shape when bent (FIG. 4B). The hose valve (FIGS. 5 and 5A) comprises a housing (24B) with a pivotable obturator (24C) which closes off the valve when it is bent to one side, thereby enabling the hose valve to be operated with one hand so as to avoid the need for the DP to touch the hose. The handle extension may have a valve (FIG. 6) with a screen (18E) therein to catch particles to prevent them from being sucked further down the instrument or into the hose. The hose valve may have a foot (24Q—FIG. 8A) to enable it to catch on the instrument holder (24R—FIG. 8) so that the instrument can be pulled off with one hand. The hose valve may have a spring-operated ball obturator (50B—FIGS. 10-10B) which automatically closes the valve or opens it when the handle extension is removed or inserted. The flange guard can have various shapes (FIGS. 16, 16B) and can be replaced by tactile circumferential elements or protrusions (FIGS. 16A, 16C-E). In lieu of a tactile element, an audible warning can be provided by means of electronic contacts (314—FIG. 17) connected to an alarm circuit (320, 322). An automatic hose valve may be implemented by providing a ring of contacts at the end of a vacuum tube so that upon insertion into the mouth, the contacts are bridged electrically by saliva, whereupon a control circuit operates a vacuum valve, whereby the DP does not have to manually touch any valve.

33 Claims, 9 Drawing Sheets

U.S. PATENT DOCUMENTS

| | | | |
|---|---|---|---|
| 2,822,808 | 2/1958 | Boone | 604/119 |
| 3,146,987 | 9/1964 | Krayl | 604/119 X |
| 3,324,552 | 6/1967 | Saffir | 433/116 |
| 3,516,160 | 6/1970 | Leffler | 433/95 |
| 3,540,432 | 11/1970 | Ayre | 604/35 X |
| 3,863,635 | 2/1975 | Swatman | 433/95 X |
| 4,081,176 | 3/1978 | Johnson | 433/95 X |
| 4,243,388 | 1/1981 | Arai | 433/27 |
| 4,397,640 | 8/1983 | Haug et al. | 433/95 X |
| 4,586,900 | 5/1986 | Hymanson et al. | 433/96 |
| 4,589,869 | 5/1986 | Wernborg | 604/902 X |
| 4,693,871 | 9/1987 | Geller | 433/116 |
| 4,723,912 | 2/1988 | Nieusma | 433/116 |
| 4,728,290 | 3/1988 | Eisner et al. | 433/116 |
| 4,776,793 | 10/1988 | La Rocca | 433/96 |
| 4,789,336 | 12/1988 | Lewis | 433/116 |
| 4,838,866 | 6/1989 | Marshall, Sr. | 604/247 X |
| 4,865,545 | 9/1989 | La Rocca | 433/96 |
| 4,872,837 | 10/1989 | Issalene et al. | 604/902 X |
| 5,013,300 | 5/1991 | Williams | 604/119 |
| 5,044,953 | 9/1991 | Sullivan | 433/91 X |

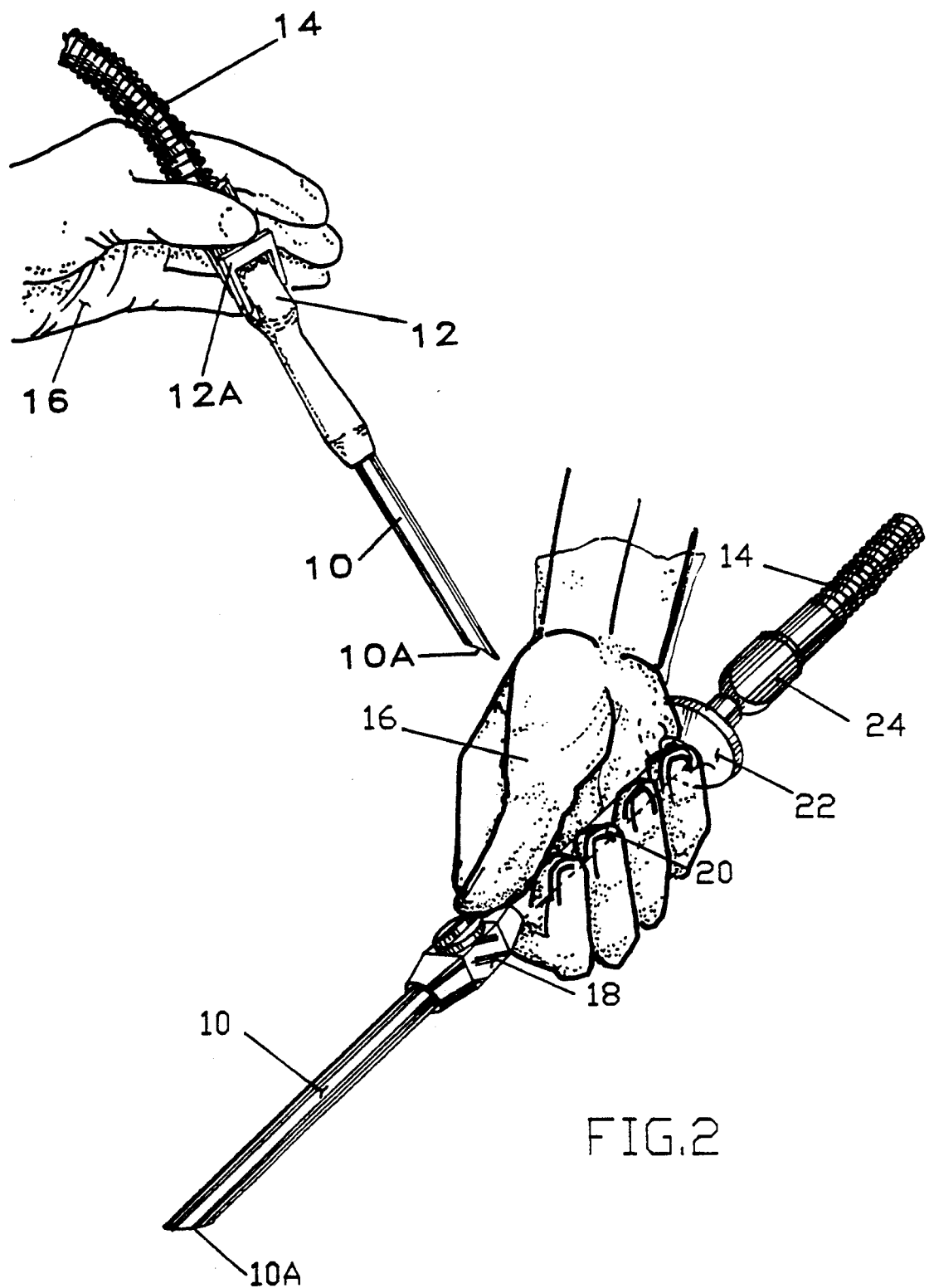

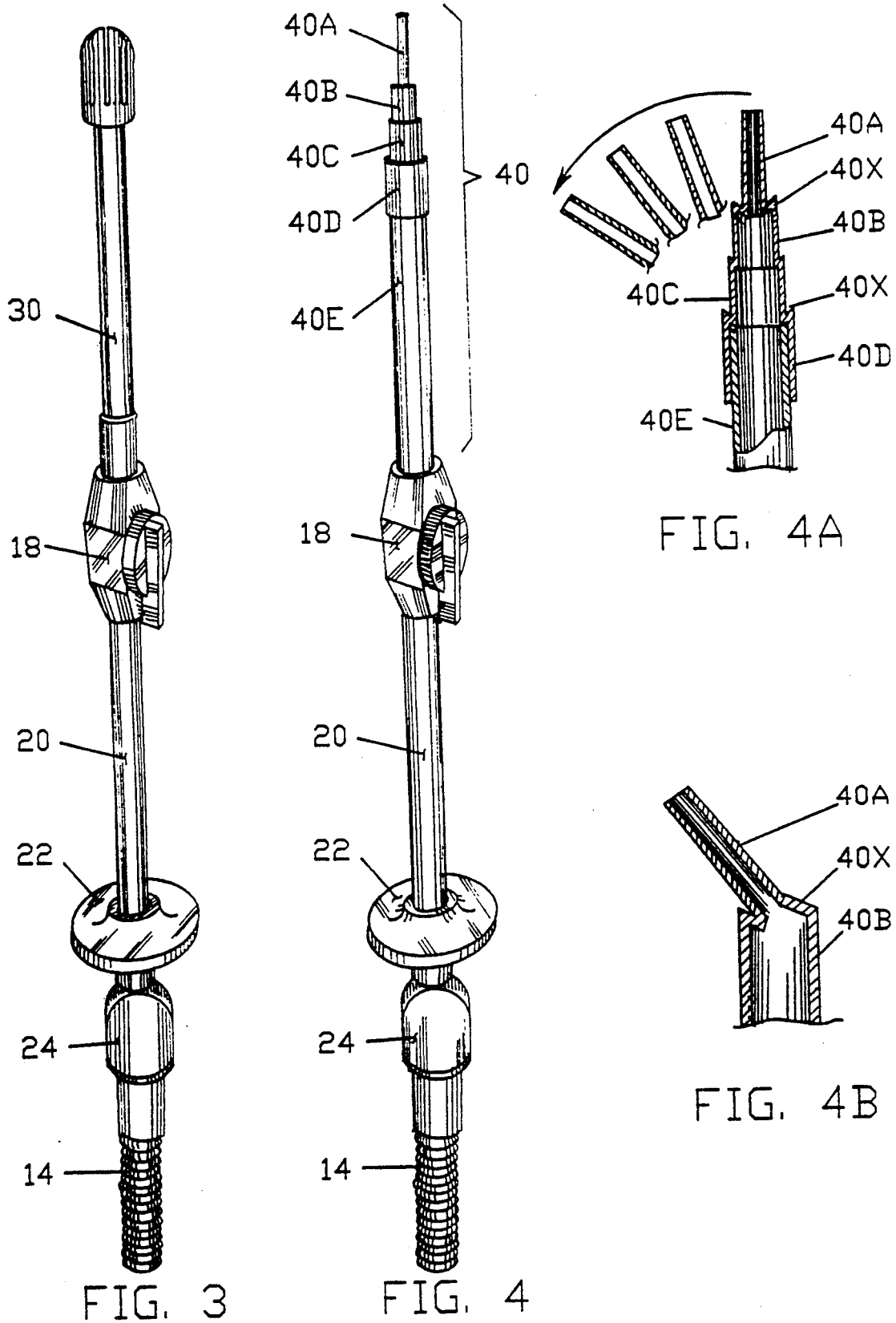

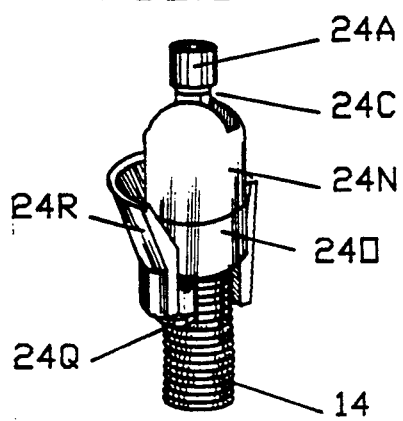
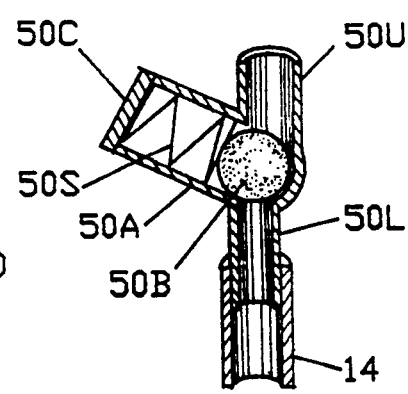
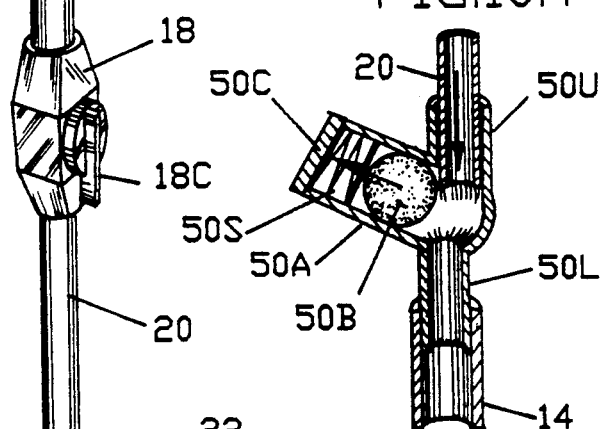
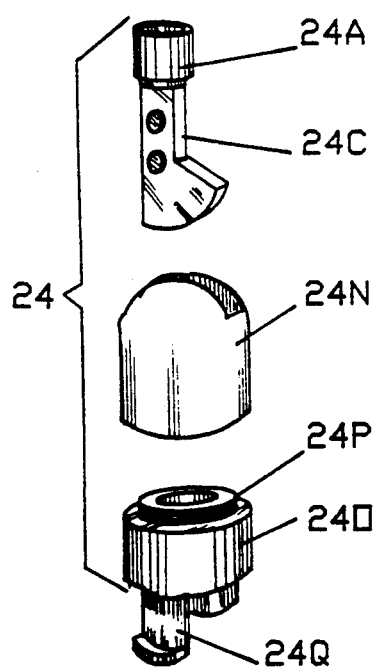
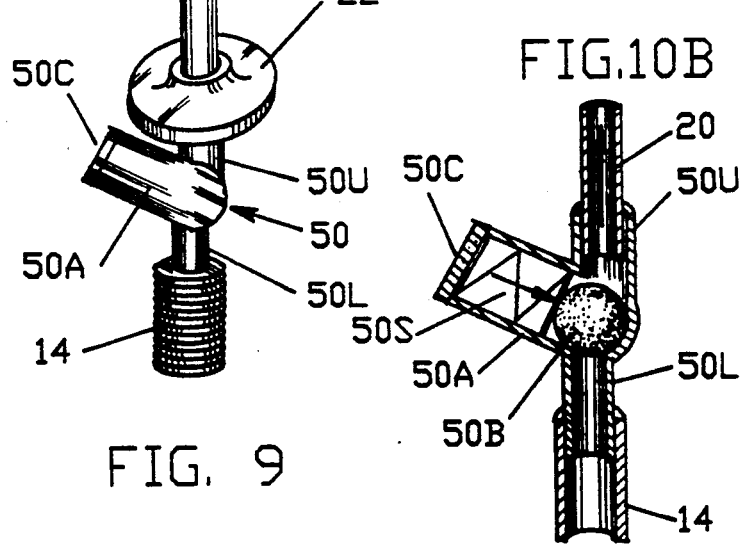

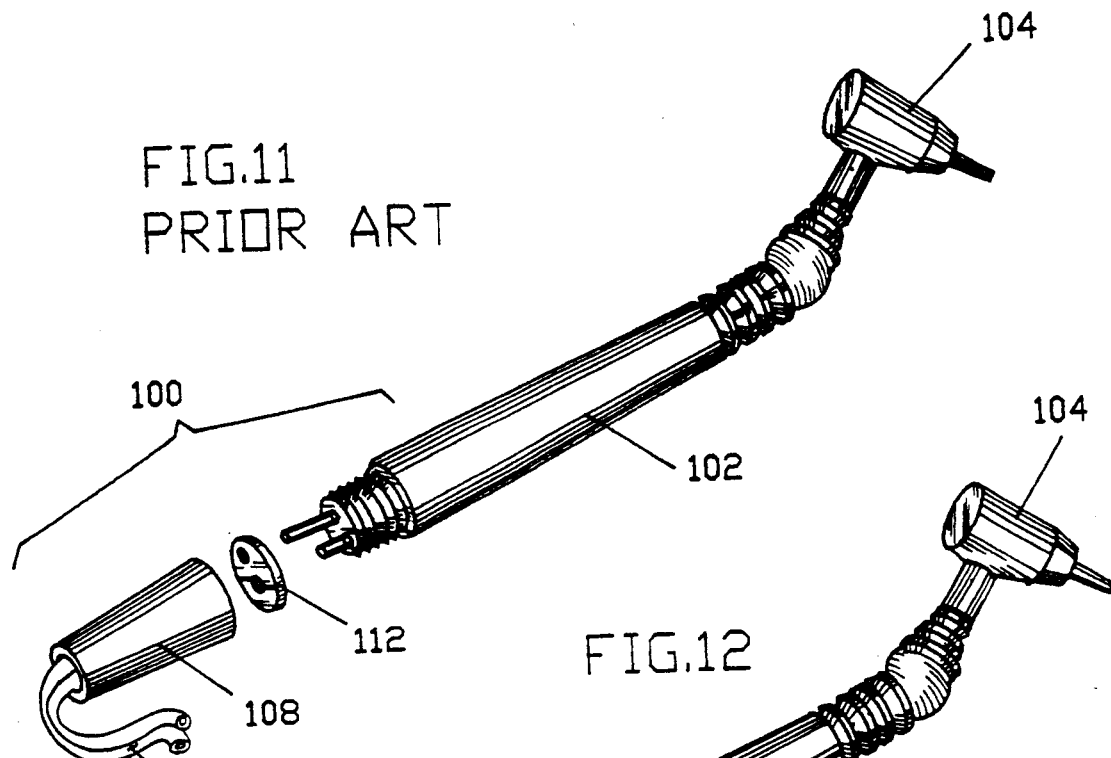
FIG.11 PRIOR ART
FIG.12
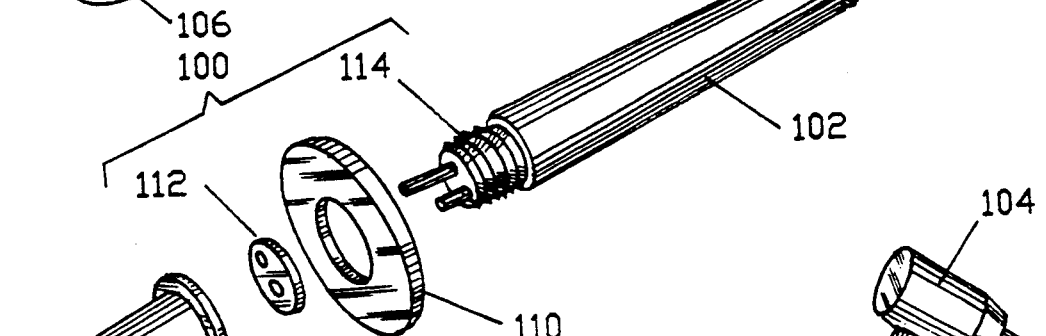
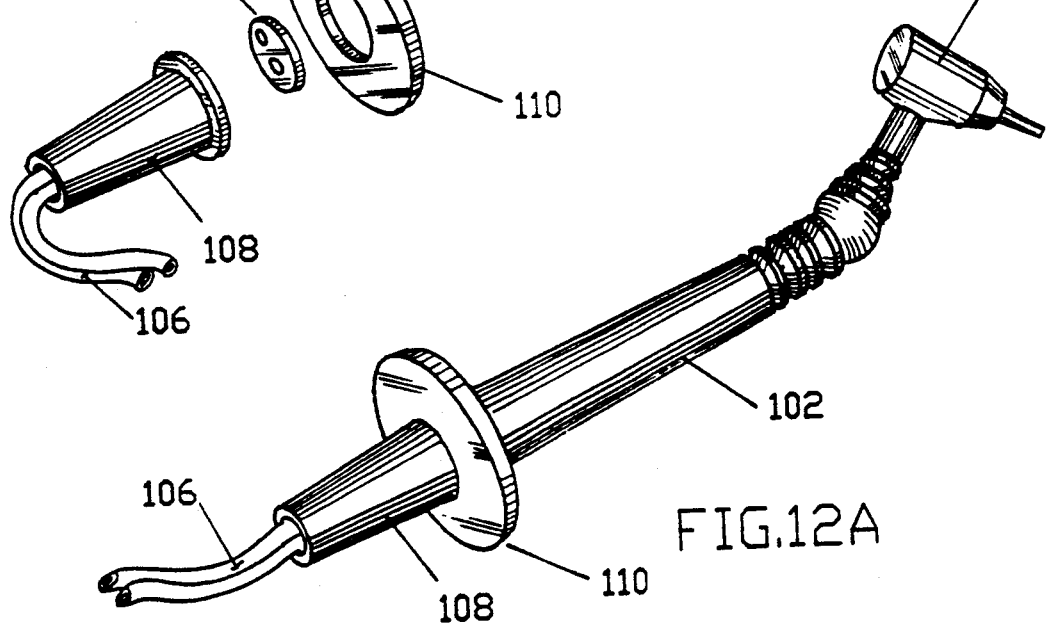
FIG.12A

ASEPTIC DENTAL VALVES AND INSTRUMENTS

This application is a continuation of Ser. No. 07/592,360, filed Oct. 3, 1990, now abandoned.

Background—Field of Invention

This invention relates generally to dental instruments, specifically to improvements in such instruments for minimizing transmission of microorganisms.

Background—Description of Prior Art

Cross-Contamination of Dental Patients by MicroOrganisms

Despite the precautions and measures taken by dentists to keep their instruments sterile, many of their practices and instruments allow undesired MicroOrganisms (MOs), including viruses, bacteria and fungi, to enter patients' mouths. These MOs generally come from other patients and are known as cross-contaminants since they travel across from one patient to another. They usually make the interpatient trip via dental instruments and their hoses, as will be shortly discussed. Cross-contamination was most undesirable in the past because it spread infectious diseases, such as influenza, colds, hepatitis, etc. However it is extremely undesirable now because of its ability to spread the lethal AIDS virus.

Ejector: In order to understand the modality of cross-contamination, refer to FIG. 1, a perspective view of a prior-art saliva and debris suction removal instrument or saliva ejector comprising a suction or High-Volume Evacuation (HVE) tube 10, its valve 12, and an attached vacuum hose 14. Tube 10 is made of plastic and has a slanted or beveled end 10A and is about 148 mm long. Valve 12 comprises a tubular body about 113 mm long and has a manually operable valve lever 12A. The proximal end of tube 10 is plugged into the distal end of valve 12 and is held by friction fit. The proximal end of valve 12 is attached to the distal end of hose 14, which usually is made of rubber and is corrugated as shown for high flexibility. The corrugations usually have a pitch or ridge-to-ridge spacing of about 4 mm and a depth of about 2 mm.

A gloved hand 16 of a dentist or hygienist (hereinafter "DP" for Dental Professional) is shown holding the instrument in the normal fashion: the fingers of hand 16 grasp valve 12 and hose 14. The DP uses the saliva ejector when necessary to remove excess saliva and debris (such as ground-away pieces of old fillings and caries or decay particles, etc.) from the patient's mouth by first operating lever 12A to open valve 12 and thereby create suction at end 10A. Then the DP inserts tube 10 into the patient's mouth and directs end 10A where necessary to suck up the excess saliva and debris.

During the foregoing operation, MOs from the patient's mouth are deposited on tube 10, valve 12, hand 16 of the DP, and hose 14. They are deposited directly on tube 10 because it is inserted directly into the mouth. They are deposited on hand 16 because it is repetitively inserted partly into the mouth where it contacts the patient's saliva directly. Also hand 16 and the instruments accumulate MOs from the airborne water mists due to splattering caused when an air-water syringe is used to rinse operative sites and other areas worked on by the DP. Hand 16 also accumulates MOs because it handles tube 10 and other dental instruments, such as scalers, curettes, pliers, etc., which are also introduced into the mouth where they pick up MOs directly. Hand 16 transfers the MOs onto valve 12 and hose 14 when hand 16 holds these parts as shown. These parts and hand 16 will also transfer the MOs onto the dentist's stand-mounted instrument holders (not shown) in which valve 12 and hose 14 rest when not in use. Thus after the DP uses the ejector of FIG. 1 on a patient, a substantial number of MOs from the patient's mouth will be deposited on tube 10, valve 12, hose 14, hand 16, and the instrument holders.

After treating the patient, the DP discards the glove on hand 16, as well as tube 10. (The DP reuses valve 12 after autoclaving [heat sterilization] or chemical sterilization.) While such disposal and sterilization eliminate many of the contaminating MOs from the patient's mouth, these procedures do not affect the MOs that hand 16 deposited on hose 14 and the instrument holders. These MOs are especially difficult to eliminate because many of them are deposited in the corrugations of hose 14. Since hose 14 is made of rubber and/or fiber, it is not possible to sterilize it by heat. While it is possible to chemically sterilize it, it is not practical to do so because chemical sterilization takes about 8 to 10 hours and the hose cannot be kept out of service that long. Similarly, it is not practicable to sterilize the instrument holders since these are permanently mounted on the dentist's stand. While heat sterilizable hoses and instrument holders have recently become available, it is awkward to autoclave hoses because they are about two meters long and it is time-consuming and difficult to remove and autoclave a hose and holders after each patient.

When the next patient is treated, the DP puts on a new pair of gloves and plugs a new sterile valve and tube into hose 14. However this will not prevent cross-contamination of the new patient from the previous patient because the DP may have to handle the instrument holder and will have to handle hose 14 again to insert the new valve and also when handling the ejector. In the process of handling hose 14 and the other parts, the DP's hand will collect and convey some of the MOs from the instrument holder and hose 14 to tube 10, which is inserted into the new patient's mouth, and also DP's hand 16 itself will be inserted directly into the new patient's mouth. As a result, a substantial number of MOs will be conveyed from the first patient to the second patient, and the third and subsequent patients. MOs from the second patient will be conveyed to the third, fourth, and so on.

As a result, many disease-causing, and even lethal, infections are transmitted between patients with current dental practices, even though precautions, such as the use of disposable gloves and disposable ejectors, are employed.

Saliva Ejector and Surgical Suction Tip: In addition to the aforementioned difficulty with the HVE tube of FIG. 1, similar difficulties occur with a saliva ejector 30 (FIG. 3) and a surgical suction tip 40 (FIG. 4).

Drill: The above cross-contamination occurs with other dental instruments. When the DP uses an air-powered drill 100, such as shown in FIG. 11 in an exploded or disassembled view for purposes to be described later, the DP's hand 16 (FIG. 1) holds the drill by its body 102 and inserts part of body 102 and the drill's head 104 into the patient's mouth. MOs from the patient's mouth thus contaminate the drill, its head, the DP's hand, and the drill's holder on the dentist's stand (not shown). When the DP is finished with the patient, the DP will disassemble the drill from its hose 106 and connector nut 108 so as to be able to sterilize the drill. In so doing, the DP invariably must handle hose 106, nut 108, and the stand mounted holder for these parts (not shown), thereby contaminating the hose, nut, and holder with the MOs from the patient's mouth. When the DP attaches a new drill onto the hose, the DP will have to handle the hose, nut, and holder again, thereby contaminating the DP's hands with the previous patient's MOs. These will be carried onto the new patient's mouth, thereby causing undesired cross-contamination.

Syringe: A similar undesirable situation occurs in the same manner when the DP uses an syringe 200 (FIG. 13) which can selectively supply air or water from a nozzle 202 under control of two valves, the operating button of one of which is shown at 204. When using this syringe, the DP cross-contaminates patients in the same manner as described supra with the ejector and valve. Because of its design, syringe 200 tends to create additional cross contamination for the following additional reasons: The syringe contains a hose valve which cannot be removed from the syringe's air-water dual-tube supply hose 206. Thus MOs which contaminate the body of valve 208 cannot be sterilized or removed easily. Also the junction 210 between valve body 208 and handle 212 of the syringe collects and serves as a trap for MOs. The syringe itself has numerous parts which make its cost high (about $220 at retail) so that dentists are reluctant to purchase enough for all of the patients they see in a day. Thus dentists tend to have fewer syringes than the number required to use a different one on every patient. This precludes them from autoclaving the syringe before use on each patient, so instead they rely on a wipe-down and chemical disinfectant, which does not provide complete sterilization. While other types of air-water syringes are available, these cannot even be disconnected from their supply hoses, so that they can be sterilized only by chemicals. Chemicals are undesirable because they are expensive, harmful to DP, harmful to the environment, unreliable since they don't sterilize the crevices of instruments, and take a relatively long time to do a complete job of sterilization.

Surgical Tip's Memory

Another difficulty occurs with tip 40 of FIG. 4. In use it is bent to a desired position to enable the DP to place its open end at an operation site. However after bending, which is done outside of the mouth before an operative procedure, the tip has a "memory" of its former straight shape and thus will tend to resume a straight shape on its own, usually when it is in use inside the mouth. Such a change in shape is undesirable since it prevents the DP from keeping the open end of the tip at the desired site. The DP must accordingly temporarily stop the operative procedure, remove the tip from the mouth, and re-bend it to the desired shape. This is time consuming, distracting, and annoying to the DP.

Vacuum Noise When Valve Removed

Another related problem which occurs in dental clinics is that of vacuum noise during the changing of valves. Referring again to FIG. 1, after the DP is finished with the first patient, the DP will, as stated, remove tube 10 and valve 12 from hose 14 to dispose of tube 10 and valve 12. Thereafter the DP will insert a new, sterile tube 10 and valve 12 into hose 14 for the next patient. However when the DP removes tube 10 and valve 12, the vacuum connected to the proximal end (not shown) of hose 14 will create a relatively loud, unpleasant, rushing sound as it enters the open end of hose 14.

This rushing sound is not normally present when tube 10 and valve 12 are installed since valve 12 can easily be turned off by its operating handle 12A. The sound can be eliminated when tube 10 and valve 12 are removed from hose 14 by turning off the vacuum at its source (not shown) or at the local shutoff hose valve at the patient's stand (not shown), but this is awkward to do since the DP may not be able to reach the switch or the shutoff valve easily. Also the switch or valve must be turned on again after the new tube 10 and valve 12 are installed, another troublesome operation. The sound can also be eliminated by installing a new valve 12 as soon as the previous one is removed, but this is not desirable since the new valve must be removed from a sterile package and it is not desirable or good surgical practice to expose a sterile valve to airborne contaminants ahead of time or for longer than necessary.

Requirement of Two Hands to Remove Valve

Another undesirable feature of the prior-art HVE assembly of FIG. 1 is that the DP must use two hands to remove tube 10 from valve 12. This is because the DP must hold valve 12 with one hand and pull out tube 10 with the other hand. (Valve 12 is then sterilized and tube 10 is discarded.) A similar problem occurs when the DP must remove a saliva ejector tube (a low-volume evacuator) or a surgical vacuum tip (top of FIGS. 3 and 4, respectively) from prior-art valve 12 of FIG. 1. The disadvantage of the requirement of two hands to disassemble the assembly of FIG. 1, or the vacuum tips of FIGS. 3 or 4, is that one hand must hold the valve and hose 14, thereby further soiling the hose with MOs from the patient's mouth.

Clogging By Debris And Requirement Of Disassembly Of Valves

Yet another problem with prior-art valves of the type shown in FIG. 1 occurs when particles, pieces, or other items from the patient's mouth are sucked into the tube and valve. Such items may be castings from a cementation procedure, such as porcelain crowns, gold inlays or onlays, etc., ground-away pieces of old fillings, etc. These pieces are sometimes waste particles which are to be disposed of, or they may be a good item, such as a crown, inlay, or onlay which has been accidentally sucked into the ejector. In either case the item creates a problem. If it is a small waste particle, it will often lodge in the internal mechanism of valve 12, thereby causing valve 12 to become inoperable. The valve must then be disassembled and the particle removed, a time-consuming and disagreeable task which exposes the DP to the contaminants in the hose. If it is a good item, it must be recovered, another disagreeable and time-consuming task. If the good item lodges in the vacuum hose, it must be blown out and recovered, a laborious job. If it lodges in the sedimentation trap, it must be fished out from the other debris and sterilized, another time-consuming and difficult job.

Objects And Advantages

Accordingly, several objects and advantages of the invention are as follows:
to provide a way to prevent MOs of one patient's mouth from entering other patients' mouths, to reduce the spread of infectious diseases, including the AIDS virus, in dental environments, to prevent cross-contamination of dental patients by MOs, to prevent MOs from cross-contaminating patients via dental instruments, their holders, and/or the hands of dental personnel, to avoid the need to chemically or thermally sterilize dental fluid hoses, to prevent such cross-contamination with dental ejectors, drills, valves, air-water syringes, etc., and to provide a viable alternative to all non-sterilizable instrument holders;

to provide a dental surgical suction tip which will not return to a straight shape after it is bent to a desired shape for operative use, and to save time, annoyance, and distraction during operative procedures;

to prevent the rushing sound which occurs when a suction tube and valve are removed from a vacuum hose, to avoid the need to turn off the vacuum at its source or the hose valve during this operation, to avoid the need to turn on the valve or source again after a new valve is installed, and to avoid any delay associated with the re-turn-on of the source;

to provide dental suction tubes and instruments which can be disassembled with one hand and without the use of two hands, thereby to further reduce soiling of vacuum hoses with MOs from the patient's mouth; and to prevent particles which are sucked from the patient's mouth from lodging in the valve and to prevent good particles from lodging in the sediment collector, to avoid the need to disassemble the valve due to particles lodging therein, to avoid the need to remove particles from the vacuum hose or the sediment collector, and to avoid the need to sterilize good pieces which have been recovered from a sediment collector or hose.

Other objects are to prevent the above-noted cross-contamination in non-dental areas, to provide a flange or tactile protrusion element for dental instruments which prevents or warns DP not to touch certain components, to provide visual, tactile, and audible warning mechanism for this purpose, and to provide an automatically starting suction tube so that the DP will not have to touch any valves at all.

Further objects and advantages will become apparent from a consideration of the ensuing description and the accompanying drawings.

DRAWING FIGURES

FIG. 1 is a perspective view of a prior-art ejection valve and attached vacuum HVE hose with a suction tip and a gloved hand holding the valve and hose.

FIG. 2 is a perspective view of an assembly similar to FIG. 1, but with a valve in accordance with a preferred embodiment of the invention. FIG. 2A is an exploded view of the assembly of FIG. 2. FIG. 2B is a longitudinal sectional view of the assembly of FIG. 2.

FIG. 3 is a perspective view of an assembly similar to FIG. 2, but with a saliva ejector tip instead of an HVE tip.

FIG. 4 is a perspective view of an assembly similar to FIG. 2, but with a surgical tip instead of an HVE tip. FIG. 4A is a sectional view of the tip of the assembly of FIG. 4 showing it in normal and successive bent positions. FIG. 4B is a close-up sectional view of one section of the tip of FIG. 4 illustrating how it bends at one of its steps.

FIG. 5 is a perspective view of a two-piece vacuum hose valve in accordance with another embodiment of the invention. FIG. 5A is a similar view as FIG. 5, but with the valve in a closed position. FIG. 5B is an exploded view of the valve of FIG. 5.

FIG. 8 is a perspective view of a three-piece vacuum hose valve which includes a locking foot to facilitate one-hand ejector tip removal, together with a holding socket on the instrument holder stand in accordance with another embodiment of the invention. FIG. 8A is an exploded view of the valve of FIG. 8.

FIG. 9 is a perspective view of a HVE valve assembly with a ball hose valve in accordance with another embodiment of the invention.

FIG. 10 is a sectional view of the ball hose valve of FIG. 9 in a closed position without the HVE tube. FIG. 10A is a similar view but with the valve in an open position with the HVE tube inserted and FIG. 10B is a similar view with the valve in a re-closed position with the HVE tube being withdrawn.

FIG. 11 is an exploded perspective view of a prior-art dental drill assembly.

Figure 12B:
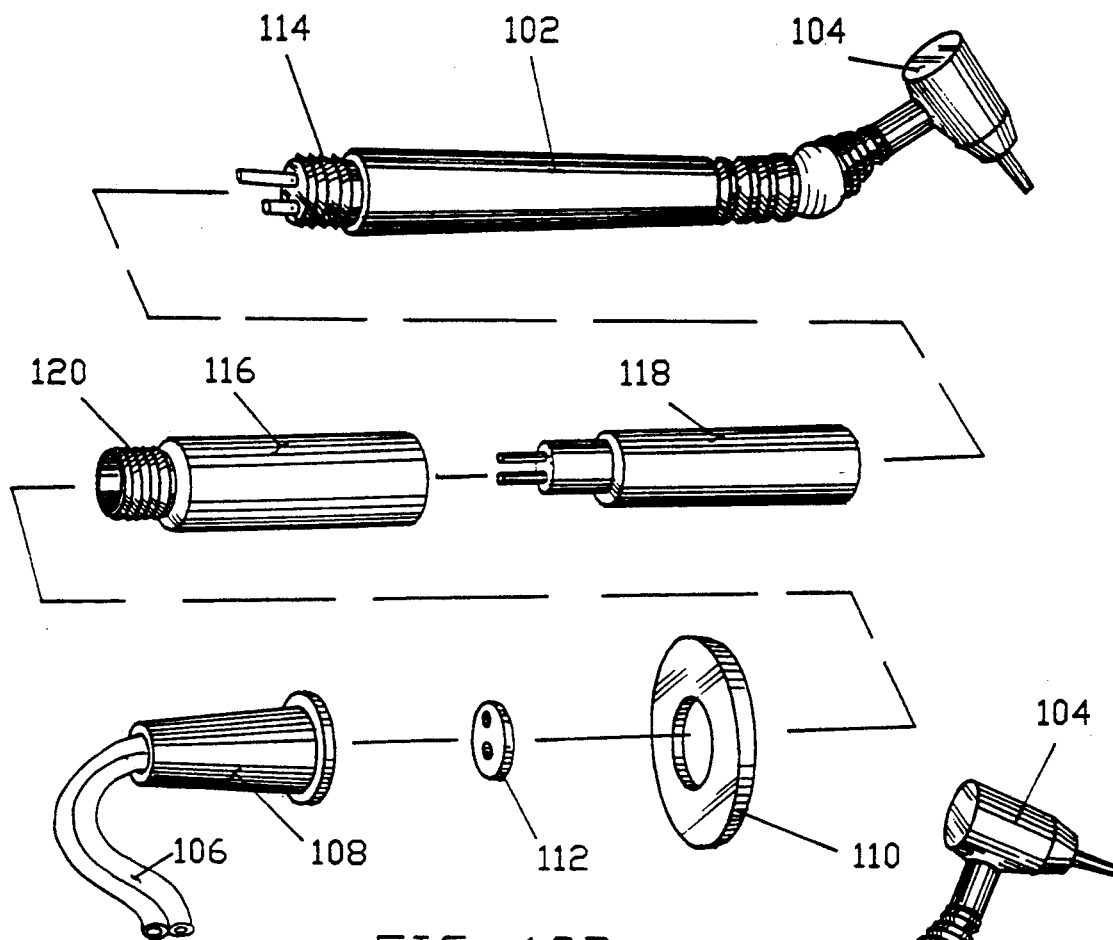
Figure 12C:
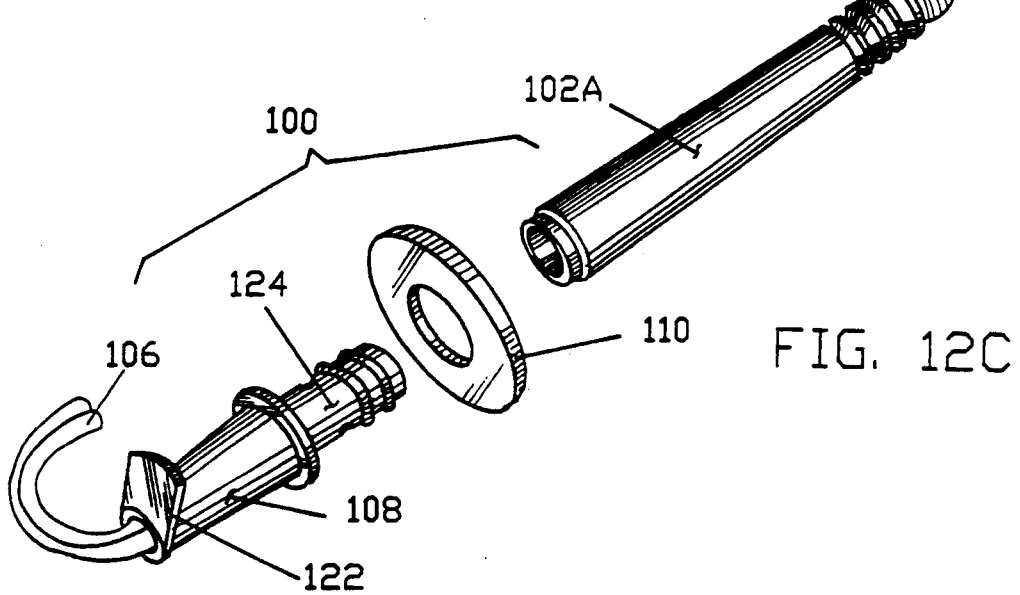

FIG. 12 is an exploded perspective view of the dental drill assembly with a flange according to the invention. FIG. 12A is a perspective view of the dental drill of FIG. 12 after assembly. FIG. 12B is an exploded view of a dental drill assembly with a flange and handle extender according to the invention. FIG. 12C shows an exploded view of the drill with a locking foot.

Figure 13:
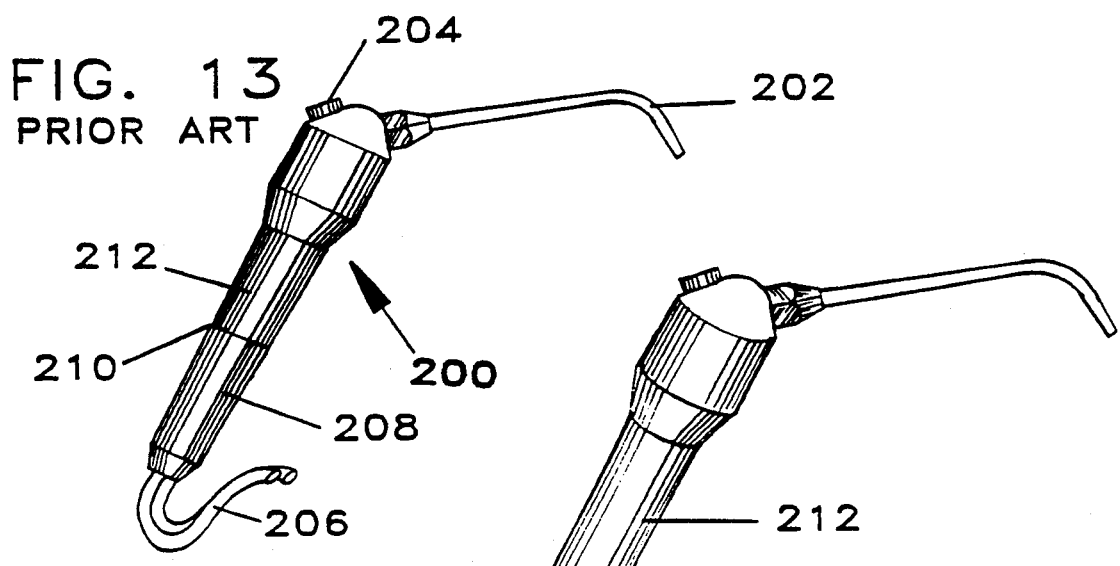

FIG. 13 is a perspective view of a prior-art air-water valve assembly.

Figure 14:
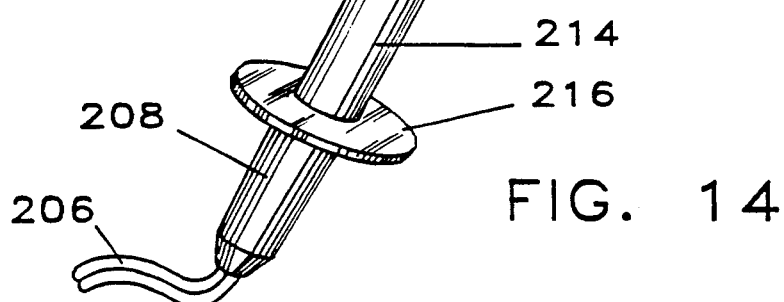
Figure 14A:
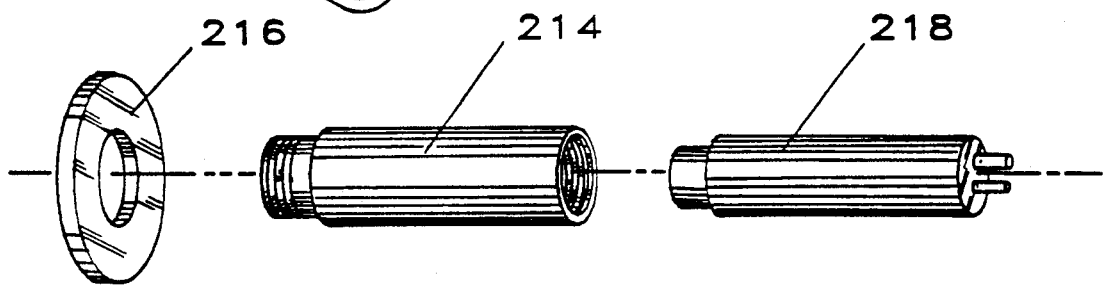

FIG. 14 is a perspective view of an air-water valve assembly with a flange and handle extender according to the invention. FIG. 14A is an exploded view of the handle extender and flange.

Figure 15:
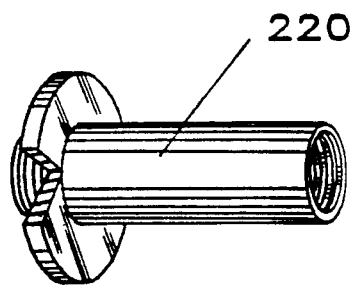

FIG. 15 is a perspective view of an alternative handle extender and flange.

Figure 16:
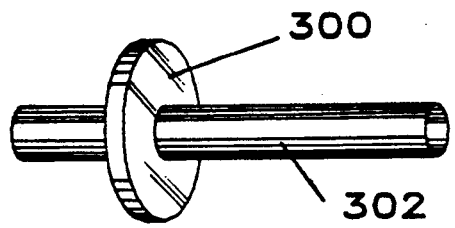

FIG. 16 is a perspective view of a Tactile Circumferential Element (TCE) in the form of a flange according to the invention. FIGS. 16A to 16E are perspective views of alternative TCEs in accordance with the invention.

Figure 17:
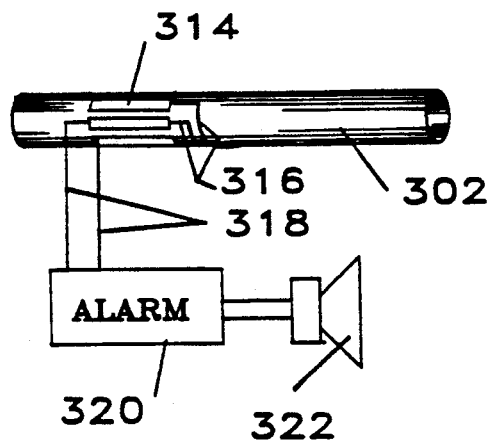

FIG. 17 is a diagram, partially in schematic form, of electronic warning device for use in lieu of the TCE in accordance with the invention.

Figure 18:
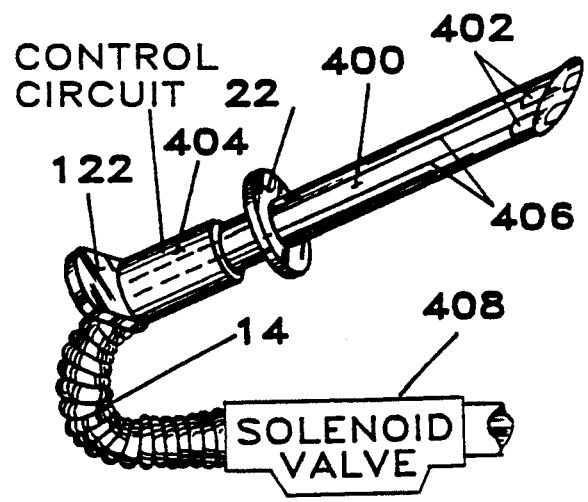

FIG. 18 is a side view of a system with an automatic hose valve in accordance with the invention.

DRAWING REFERENCE NUMERALS

10 HVE suction tube 10A tip
12 valve 12A handle
14 vacuum hose 16 hand
18 valve 18A cylinder
18B bore 18C handle
18D valve extension tube 18E screen
18F modified valve 18G side handle portion
18H crossover bar
20 handle extension 22 flange guard
22A through hole of flange guard 22B, 22C support extensions
24 hose valve 24A hosel
24B body 24C obturator
24D hosel 24E recess
24F slot 24G bore
24H pivot 24I bosses 24J bore 24K obturating area
24L detent bosses 24M valve closed recesses
24N upper body 24O lower body
24P flange 24Q footed leg
24R instrument holder
30 saliva ejector
40 surgical suction tip 40A-E sections of 40
40X integral annular portion 50 automatic hose valve
50A body 50B ball obturator
50C cap 50L lower hosel
50S spring 50U upper hosel
100 drill 102 body of 100
102A body of alternative drill 104 head of 100
106 hose of 100 108 connector nut of 100
110 flange guard 112 washer
114 screw threads 116 sleeve
118 conduit body 120 screw threads
122 locking foot 124 quick disconnect
200 syringe 202 nozzle
204 button 206 hose
208 valve body 210 junction
212 handle 214 handle extension
216 flange guard 218 insert
220 integral handle and flange
300 flange guard 302 handle extension
304 ring of nubbins 306 dome flange guard
308 castellated cylinder 310 pyramids
312 scored ring 314 contact
316 jumper 318 leads
320 alarm circuit 322 speaker
400 HVE tube 402 ring of contacts
404 control circuit 406 leads
408 solenoid valve

ABBREVIATIONS

AWV air-water valve DP dental professional
HDPE high density polyethylene TCE tactile circumferential element
HVE High volume ejector MO microorganism
DSVA disposable suction valve assembly

Figures 2A, 2B:
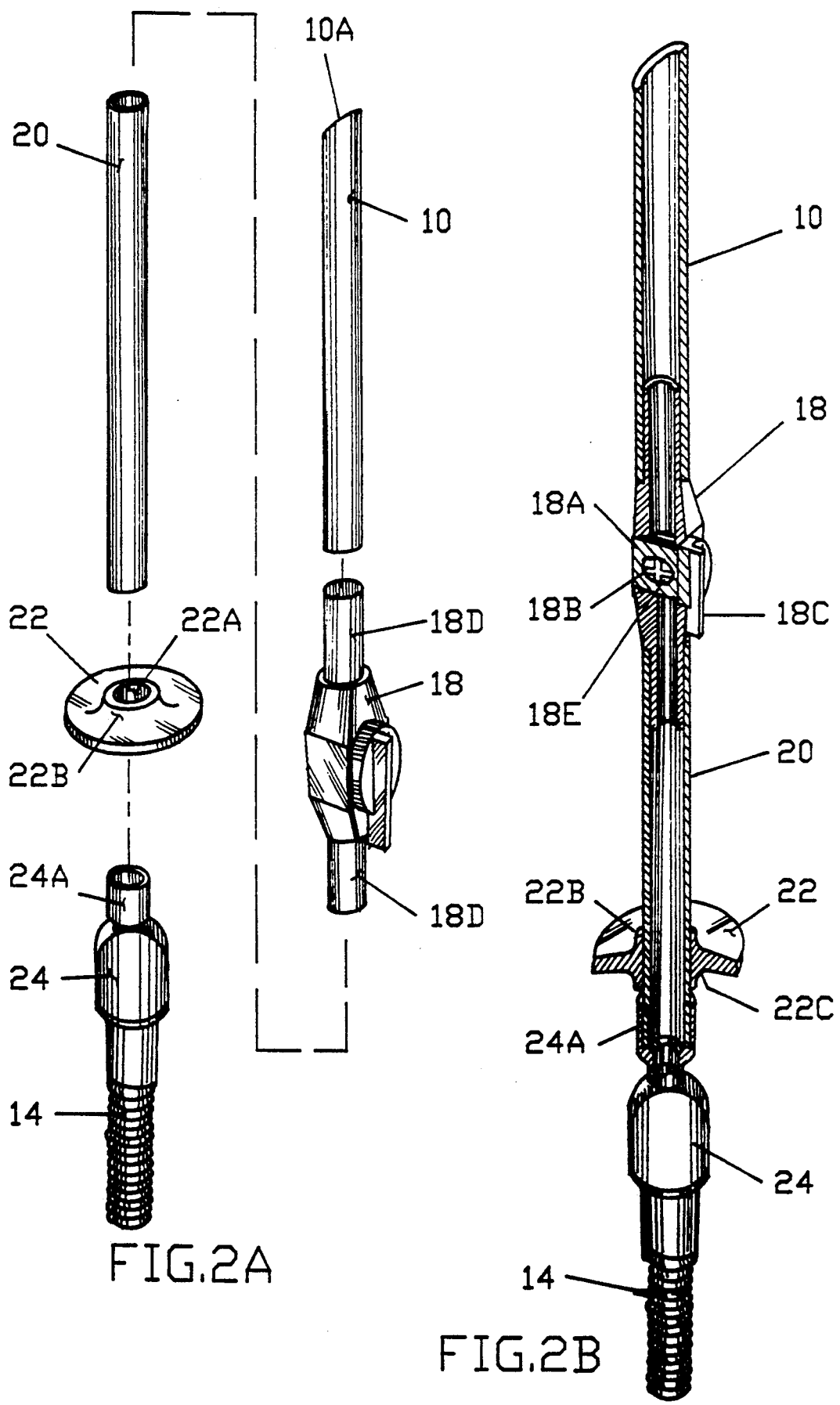

Description—FIGS. 2 to 2B—Flange Guard And Handle Extension

In accordance with a first embodiment of the invention, we have substantially overcome the problem of cross-contamination of dental patients by MOs, discussed above in connection with FIG. 1, by providing a valve with a handle extension and flange guard in place of valve 12 of FIG. 1. This handle extension and flange guard prevent DP from grasping and hence contaminating hose 14 and thereby prevent cross-contamination of patients by MOs.

As shown in FIG. 2, suction tube 10 is connected to hose 14 via a valve 18, a handle extension 20, a flange guard 22, and a hose valve 24, in lieu of valve 12 (FIG. 1).

Valve 18, shown in more detail in FIGS. 2A and 2B, is a standard barrel valve which has a rotatable cylinder or barrel 18A which has a bore or through hole 18B and an external handle 18C. When handle 18C is turned manually so that it is parallel with the axes and lumens of tubes 18 and 20, barrel 18A will be in the position shown (FIG. 2B) where bore 18B is parallel to these axes and lumens. Thus barrel 18A will allow passage of fluid through these lumens and the valve will be on. When handle 18C is perpendicular with the lumens of tubes 10 and 20 (not shown), barrel 18A will be at 90° to the position shown. Bore 18B will be perpendicular to these axes and lumens and will thus not allow fluid to pass through these lumens. Valve 18 is preferably made of high-density polyethylene and is about 57 mm long, overall. Each end of valve 18 has male connecting sections 18D about 10 mm long. Tube 10 is plugged onto distal section 18D where it is held by force fit.

Handle extension 20 is 127 mm long, 11 mm in outside diameter, and is similar to tube 10, except that it has a perpendicular, rather than a beveled distal end. Its distal end is plugged onto the proximal connection section 18D of valve 18 and is held by force fit. Its proximal end is plugged into a hosel or connector 24A on valve 24.

Flange guard 22 comprises an annular member with a through hole 22A. It has outwardly tapering or bulging center support or alignment extension areas 22B and 22C on its opposite sides, surrounding bore 22A. The diameter of bore 22A is slightly less than 11 mm so as to have a force or friction, but sliding, fit onto handle 20. The diameter of flange 22 is 32 mm. Thus flange 22 protrudes outwardly from handle extension 20 about $(32-11)12=10.5$ mm. Guard 22 is positioned at the proximal or base end of handle 20, so that its proximal support extension 22C is adjacent hosel 24A.

Tube 10, valve 18, handle 20, and flange 22 can be economically made so as to be disposable after one use. These components constitute a Disposable Suction Valve (DSV) assembly.

Hose valve 24 is shown in more detail in FIG. 5 and will be discussed later in conjunction with that FIG. Suffice it to say here that valve 24 is normally on during an operative procedure but can be manually shut off so as to block air from rushing into vacuum hose 14 and creating a loud sound when the DSV assembly is removed from valve 24.

In lieu of tube 10, a saliva ejector tip 30 (FIG. 3) can be attached to valve 18. Tip 30 has a strainer at its distal end.

Operation—FIGS. 2 to 2B

In operation, the DP uses the DSV Assembly (DSVA) as follows: The DP holds the DSVA with one hand 16 (FIG. 2) around tube 10, valve 18, and handle 20. The DP uses the DSVA in the normal manner, after turning on valve 18, to suck excess saliva and debris from the patient's mouth. Thereafter the DP closes valve 18 and returns the DSVA to its holder (not shown) on the dental stand (not shown).

The DP has ample room to hold the DSVA without touching hose 14 since the combined length of tube 10, valve 18, and handle 20 are about 300 mm, much longer than the width of an adult's hand, which is about 100 mm. Thus the provision of handle extension 20 enables the DP to handle the valve and HVE suction tube without handling the non-sterilizable or difficult-to-sterilize hose. Although such handling will carry MOs from the patient's mouth to the parts of the DSVA, such contamination will not matter since these parts will be discarded after use and since the DP will not handle hose 14 at any time.

Flange guard 22 prevents the DP from handling the hose since guard 22 will block the DP's hand from sliding down to the hose. In effect, it creates a tactile barrier to prevent the DP from inadvertently touching the hose. The guard also provides a visual indicator so that when the DP first extends a hand to grasp the DSVA, the DP will see guard 22 and be reminded to grasp it only on the distal side of the flange. Grasping it on the proximal side of the flange (where the DP could touch the forbidden hose) will be difficult and awkward since the DSVA will be sitting in its holder with guard 22 resting on the holder, which will block any attempt to grasp the hose.

Thus the reader will see that by providing flange guard 22 and handle extension 20, we have provided a HVE suction valve and tube assembly which will prevent the DP from handling the hose and thus reduce drastically cross-contamination of patients by MOs which are transferred over the hose when the DP handles such hoses during use of the HVE suction tube.

FIG. 3—Saliva Ejector

In lieu of HVE tube 10, a saliva ejector tip 30 (FIG. 3) can be attached to valve 18. The same advantages accrue when using saliva ejector tip 30 as with HVE tube 10.

Description—FIGS. 4-4B—Surgical Tip

In lieu of a HVE tube or a saliva ejector, a surgical suction tip 40 (FIG. 4) can be used with valve 18 and handle extension 20. Tip 40 has a very small aperture at its distal end for fine suction applications, such as when performing surgery, e.g., when the DP must vacuum a drilled-out cavity in a tooth, or a tooth socket in the jawbone. Tip 40 has four integral sections at its distal end: these sections have gradually increasing diameters, proceeding toward its proximal end, and are joined by a series of respective steps. Starting from the distal end, a fine tip end section 40A is about 26 mm long and has an internal diameter (ID) of about 2 mm. A second section 40B is about 11 mm long and has an ID of about 4.5 mm. A third section 40C is about 11 mm long and has an ID of about 8 mm. A fourth section 40D is about 14 mm long. Section 40D telescopingly friction fits over a fifth section 40E which is about 76 mm long and which has an ID of about 8.5 mm. Section 40E is similar to handle extension 20 of FIG. 2A. Sections 40A and 40B are joined by an integral annular portion 40X which forms the first step and whose radial measurement from the outside of section 40A to the inside of section 40B is about 1 mm (FIGS. 4A and 4B). Sections 40B and 40C are joined by similar annular sections, as are sections 40C and 40D. The wall of each section and annular portion 40X has a thickness of slightly less than 1 mm. Tip 40 preferably is made of high-density polyethylene.

Operation—FIGS. 4-4B—Surgical Tip

The surgical tip of FIGS. 4 to 4B has the same advantages regarding asepsis and operates in the same manner as the tips of FIGS. 2 and 3. As noted supra, however, its predecessor had an undesirable memory in that, after being bent to a desired shape for an operative procedure, it will gradually return to a straight shape as shown in FIG. 4.

The tip of FIG. 4 remedies this disadvantage as follows: Since each pair of adjoining sections is joined by an annular step-forming section 40X, as shown best in FIG. 4B, when one section is bent with respect to the next, annular section 40X will kink and retain the bend. As shown in the phantom views at the top of FIG. 4A and in FIG. 4B, when section 40A is bent to the left, the left side of annular section 40X, which is the inside of the bend, will kink downwardly as shown on the left side of FIG. 4B. At the same time the right or outer side of annular section 40X will kink upwardly, as shown.

This kinking action will not self-reverse, as will mere bending of a plain section, so that when any section is bent with respect to the next lower section, the bend will maintain itself. In fact we have found that the bend can be made over any range, from about 0° to about 45° and it will maintain itself at whatever angle in this range is chosen.

By bending each of the three joints, a large and permanent bend of up to about 135° can be made. This bend will hold itself in position and will not reverse itself or gradually straighten, as with prior-art surgical tips. Thus once a bend is made, the DP can continue to use the tip without the annoyance of having to periodically rebend it, as had to be done before.

Figure 5:
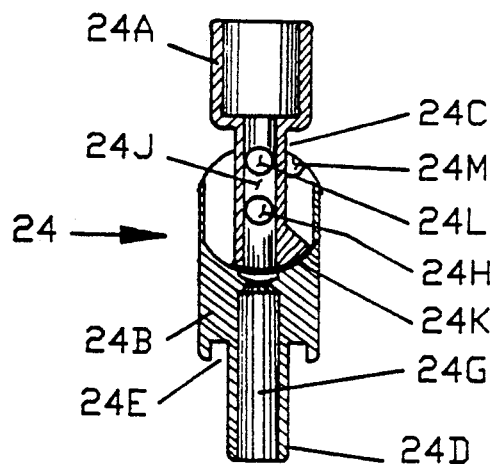
Figure 5A:
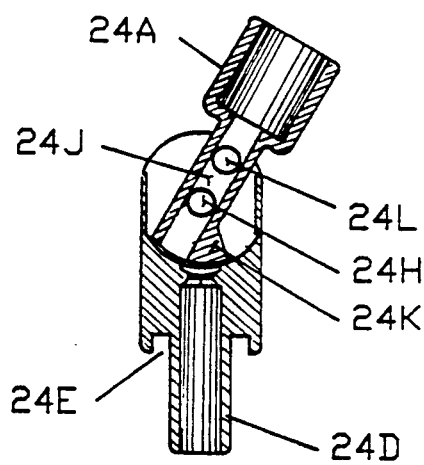
Figure 5B:
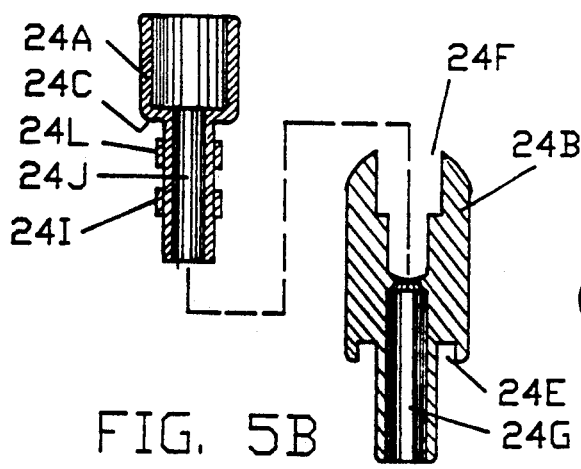

Description—FIGS. 5-5B—Hose Valve

It is advantageous to use hose valve 24 of FIGS. 1 to 4, shown in detail in FIGS. 5 to 5B, in conjunction with the flange guard and handle extension of FIGS. 1 to 4 since it permits the DP to turn off the vacuum to the suction assembly with one hand and thereby avoid touching and contaminating hose 14. Valve 24 has only two parts: a body or housing 24B and a pivotable obturator 24C.

Body 24B is about 53 mm high and the other parts are of proportional size. Body 24B has a cylindrical shape and a lower integral hosel 24D which is coupled to hose 14 (FIG. 1) in a conventional manner, e.g., by friction fit. The sides of the body extend down around but spaced from hosel 24D to form an annular recess 24E into which the hose is inserted and which can be rested upon the instrument holder of the dental stand (not shown). The top of body 24B has a curved, dome-shaped configuration with a slot 24F (FIG. 5B). The body also has a bore 24G running therethrough from hosel 24D to slot 24F.

Obturator 24C is pivotably mounted within body 24B and protrudes therefrom via slot 24F. It is an elongated member which is pivotably mounted or hinged within slot 24F at a hinge or pivot 24H. Hinge 24H comprises a pair of bosses 24I (FIG. 5B) protruding from opposite sides of the obturator's body in opposite directions and a pair of mating recesses in the walls of the slot 24F. The obturator also has an axial bore 24J therethrough. Its top is constituted by upper hosel 24A and its bottom has a curved obturating area 24K. The obturator also has a pair of detent bosses 24L on opposite sides thereof, above hinge bosses 24I. Bosses 24L mate with either of two pair of detent recesses in the walls of slot 24F, above the hinge bosses. One pair, directly above hinge 24H, are valve-open recesses, and another pair 24M (FIG. 5) are to one side of the valve-open recesses are valve-closed recesses.

Operation—FIGS. 5-5B

The obturator can be pivoted from an open or transmissive position which is coaxial with the valve's body, as shown in FIG. 5, to a closed or non-transmissive position where it makes about a 30° angle with the body's axis (FIG. 5A). When the obturator is in the open position (FIG. 5), air and other fluids can move through the valve via bore 24G in the body and bore 24J in the obturator's body since both bores communicate and are coaxial. The obturator is held in the open position by the cooperating detent bosses 24L and their mating valve-open detent recesses. The obturator can be pivoted past the holding force of this detent by a slight effort to its closed position (FIG. 5A), where its bosses are held by similar valve-closed detent recesses 24M. In the closed position, bore 24G in the body is stopped or obturated by obturating area 24K of the obturator; i.e., the bores of the obturator and body are at an angle so there is no communication therebetween. Thus the valve is non-transmissive in this position.

The valve can be easily turned off or on by simply pivoting obturator 24C from its coaxial position (FIG. 5) to its angled position (FIG. 5A). Such pivoting can easily be done with one hand when disposable suction valve assembly (DSVA) 10-18-20 of FIG. 2 is inserted into the hose valve of FIG. 5 and the hose valve is resting in the dental stand (not shown). Using one hand—the instrument holder in the stand provides the other "hand"—the DP simply pivots the DSVA with respect to the hose valve assembly from the on to the off position, or vice-versa. Thus the DP does not have to even touch the valve or the hose in order to turn the hose valve on or off. As indicated above, the DP normally turns the hose valve off when changing the DSVA so that the vacuum sucking noise will not be heard when the DSVA is removed.

The DSVA itself can be removed or replaced with one hand also by simply plugging it into hosel 24A of the hose valve, or pulling it out. When plugging it in, the instrument holder will hold the hose valve, and when pulling the suction valve assembly out, the weight and consequent intertia of the hose will hold the hose valve, or an extension foot (FIG. 8A) can be added to the hose valve to hold it in against an oblique, angled upward pull.

Figure 6:
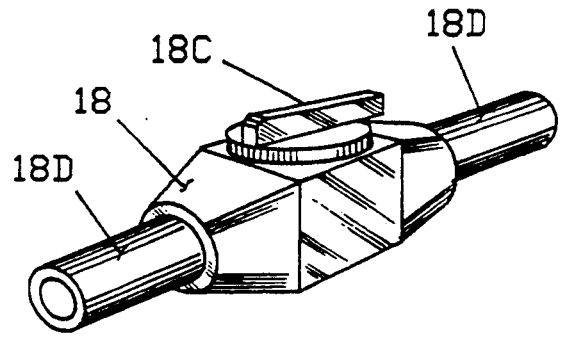
FIG. 6 is a perspective view of a lever-operated drum valve in accordance with another embodiment of the invention.
Figure 6A:
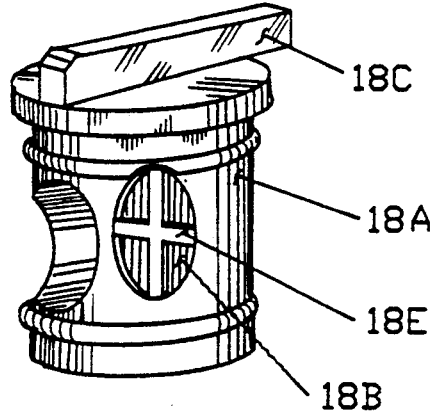
FIG. 6A is a perspective view of a rotatable body with a built-in screen filter in the valve of FIG. 6.

Description—FIGS. 6 & 6A—Valve With Filter

Valve 18 of FIGS. 2 to 4 is shown in perspective view in FIG. 6. As stated, the valve consists of an outer housing and an internal barrel or cylinder 18A (FIG. 6A) which is rotatably mounted in the housing on suitable pivot rings which snap into and mate with corresponding grooves in the housing. When handle 18C is in the position shown, where it is coaxial with the valve's axis, i.e., with the axis of extension or joining tubes 18D, barrel 18A of the valve will be in a position so that bore 18B of the barrel is aligned with the bore through the valve's body and extension tubes 18D. Thus the valve will be open or transmissive of fluids therethrough. When the DP turns handle 18C so that it is perpendicular to the valve's axis (not shown), then bore 18B also will be perpendicular to the valve's axis so that the valve will be off or non-transmissive.

In accordance with the invention, we provide a screen 18E within bore 18B. Screen 18E consists of a pair of elongated orthogonal members which extend across the bore so as to divide the bore into four quarter-circle passages, each of which has far less area than the original bore. Screen 18E preferably is molded with the barrel and is in the center of the longitudinal axis of the bore. If any particles, such as pieces of old fillings, are sucked into tube 10 (FIG. 1), they will be trapped by and lodge against screen 18E, rather than lodging in the hose, the hose valve, or the sediment trap. If they block the flow of fluids through the suction tube assembly, they can easily be removed from valve 18 by disassembling the HVE suction assembly and shaking or poking the particles out. In this manner the DP does not have to handle the uncontaminated parts, such as the hose and the hose valve, to remove the unwanted particles.

The screen can alternatively be molded in the housing in its distal portion (not shown). In this way the particles can be shaken out without disassembling valve 18A.

Figure 7:
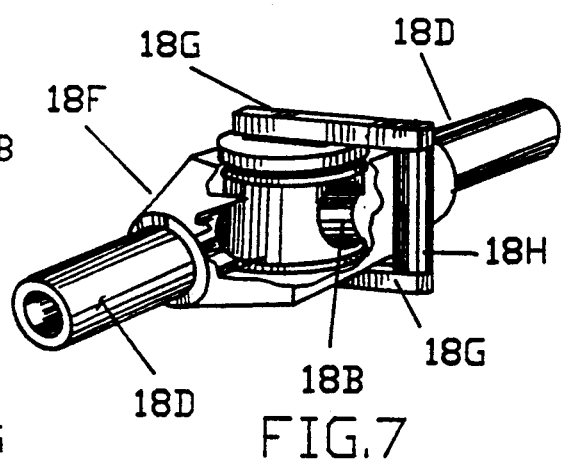
FIG. 7 is a perspective cutaway view of a handle-operated drum valve similar to that of FIG. 6.

FIG. 7—Valve With Bar Handle

Valve 18F of FIG. 7 is similar to that of FIG. 6, except that its handle has respective side portions 18G which are attached to both ends of cylinder 18A. The ends of side portions 18G distal from the valve are joined by a crossover bar portion 18H so that the handle spans the width of the entire valve. The handle of FIG. 7 is easier to operate than handle 18C (FIG. 6) since its crossover bar 18H can easily be moved with the DP's thumb. Thus there is far less chance of the DP having to use both hands and thus touch and contaminate the hose with the valve of FIG. 7. Since the crossover bar will prevent side portions 18G from being aligned coaxially with the valve and its extension tubes 18D, side portions 18G are mounted so that the valve is fully on when crossover bar 18H contacts the distal one of tubes 18D, i.e., the bar is rotated maximally forward, and the valve is fully off when bar 18H contacts the proximal one of tubes 18D, i.e., the bar is rotated maximally backward.

Description—FIGS. 8 & 8A—Hose Valve With Retaining Foot

The hose valve of FIGS. 5-5B, which is also shown at 24 in FIG. 2, preferably is modified so that the DSVA (10-18-20 of FIG. 2) can be removed with one hand when the hose valve is held by an instrument holder on the dentist's chairside stand. The modified version is shown in FIGS. 8-8A.

The hose valve has a moveable obturator 24C with an upper hosel 24A. The body portion is formed in two parts: upper part 24N and lower part 24O. Upper part 24N is identical to the upper part of body 24B (FIG. 5) and operates similarly with obturator 24C. Lower body part 24O comprises a cylindrical member with an upper annular flange 24P (FIG. 8A) which engages a circumferential internal protrusion (not shown) in upper part 24N. An "O" ring (not shown) is positioned between the lower and upper body parts to complete the seal. Lower part 24O can swivel around upper part 24N; this makes the drag and twist of the hose less tiring while the DP holds the DSVA.

The bottom of lower body part 24O has a footed leg 24Q which extends directly down and has a short foot which extends perpendicular to the axis of the valve and its bore. Footed leg 24Q is about 17 mm long and its foot is about 5 mm long and which protrudes outwardly beyond the outside surface of lower body portion 24O. When lower body part 24O is attached to upper body part 24N, the resulting body part is identical to body part 24B of FIG. 5, except for the addition of footed leg 24Q.

The hose valve, with hose 14 attached (FIG. 8) is held, when not in use, in an instrument holder 24R (FIG. 8) which is attached to a vertical surface of a chairside dental stand (not shown). Holder 24R comprises a cylindrical member with an open front area. The cylindrical member has an upper funnel-shaped portion which converges to the central axis of the holder and a lower plain-cylinder portion which is parallel to the axis. The rear side (not shown) is attached to the dental stand, preferably by a standard holder bar (not shown). The lower portion has two parts, an upper part with an internal radius which is the same as that of lower body 24O, and a lower part with an internal radius which is about 2 mm less than that of lower body 24O. The two parts are separated by an upwardly facing ledge; the bottom of the hose valve rests on this ledge.

Alternatively the holder can be made without a ledge, in which case the hose valve may be held therein by making its upper part 24N diverging upwardly so that it cannot pass through the holder. In this case the hose valve would sit lower in the holder and footed leg 24Q would be shortened so that its foot extends just under the bottom of the holder when the hose valve is seated in the holder.

In use, when the DP is finished using the DSVA, the DP first turns off valve 18 (FIG. 2) and returns it to holder 24R by first inserting hose 14 into the open front of the holder with the hose valve about several centimeters above the holder. The DP can do this with one hand without touching the hose valve or the hose, i.e., the DP can keep his or her hand solely on the portion above flange guard 22 (FIG. 2) at all times. Then the DP lowers the entire assembly so that the hose valve will proceed into the upper funnel portion of holder 24R and will come to rest upon the aforementioned ledge in the lower portion. While so lowering the assembly, the DP must turn it so that footed leg 24Q faces out so that it will proceed through the front open area of the holder. Once it comes to rest in the holder, the DP can turn it so that the foot is under the holder as shown in FIG. 8, if the natural home orientation of hose 14 does not do this automatically. Alternatively, the DP can leave the assembly in a position (not shown) where foot 24Q is directly below the open front of the holder.

To use the assembly again, the DP merely rotates it so that foot 24Q is under the open front of the holder (if it is not already there) and lifts it up a few centimeters such that foot 24Q moves up through the open front. Then the DP pulls the assembly out horizontally and away from the holder so that hose 14 moves out through the open front. The hose and DSVA will now be completely free of the holder and can be used normally.

To change the DSVA to provide a new assembly for another patient, the DP first turns off the hose valve by tilting the suction valve to one side to turn off the hose valve as indicated above in conjunction with FIG. 5. Then (or before turning off the hose valve) the DP merely twists the assembly so that foot 24Q is under the closed portion of the holder as shown in FIG. 8 (if it is not already there). The DP can then pull the DSVA (FIG. 2) off by pulling it coaxially with the obturator. The hose valve will remain in the holder since the foot of leg 24Q will engage the bottom of the holder as shown in FIG. 8, which prevents the hose valve from leaving the holder. The DSVA will separate from the hose valve at hosel 24A, leaving the DSVA free for disposal and the hose valve still in the holder. No vacuum sucking noise will be heard since the hose valve is off. The DP can then insert a new DSVA in to the hosel with one hand and without holding the hose or its valve.

Thus the DSVA and can be changed with one hand without touching the hose or its valve and without hearing any suction noise.

Description—FIGS. 9 and 10-10B—Automatic Hose Valve

In lieu of the manually operable hose valve of FIG. 8, an automatically operable hose valve can be provided, as shown in FIGS. 9 to 10B. This valve closes automatically when the DP removes the DSVA (10-18-20) from the hose valve and attached hose.

An outside view of the hose valve is shown at 50 in FIG. 9. It comprises a body portion 50A which is elongated and extends at an oblique angle to the axis of the DSVA and hose 14. Attached to the upper side of body 50A is an upper hosel 50U and attached to the lower side of body 50A is a lower hosel 50L. Upper hosel 50U receives the proximal end of handle extension 20 (FIGS. 10A and 10B) by friction fit and lower hosel 50L is plugged into hose 14, again by friction fit.

Valve 50 is generally hollow on its inside, except for a ball obturator 50B and a helical spring 50S. Spring 50S and ball 50B are positioned in body portion 50A, the distal end of which from the axis of the valve is closed by a cap 50C. Spring 50S urges ball 50B to the lower right (FIG. 10) against the right side of body portion 50A. In this position, ball 50B rests over the lumen of the open upper end of hosel 50L and stops or obturates hosel 50L.

When the lower or distal end of extension 20 is inserted into hosel 50U as indicated in FIG. 10A, such lower end will cam ball 50B upwardly in the direction indicated by the arrow in FIG. 10A, against the force of spring 50S. This will force ball 50B away from the open lumen of hosel 50L to an "open" position within body 50A, thereby removing the obturation or stop over hosel 50L.

When extension 20 is removed, as indicated in FIG. 10B, spring 50S will urge ball 50B back to its closed position, as indicated in FIG. 10B.

Operation—FIGS. 9 and 10-10B

In operation, assume that extension 20 is removed from valve 50, as indicated in FIG. 10. In this position, spring 50S, gravity, and the vacuum urge ball 50B to its obturating position so that it blocks hosel 50L and hence hose 14. Thus no vacuum sound will be heard, even though a vacuum is applied to hose 14.

When the DP plugs the DSVA into hosel 50U, as indicated in FIG. 10A, valve 18 should be closed so that a sucking or hissing sound will not be heard when hose valve 50 opens. When extension 20 in plugged into hosel 50U, it will force ball 50B up as shown, thereby opening the lumen of hosel 50U and hence hose 14. However since valve 18 is closed, no vacuum sound will be heard from the tip of tube 10. The DP now uses the DSVA in the normal fashion, opening and closing valve 18 when needed. Hose valve 50 will remain open.

When the DP is finished with the current patient and desires to remove and discard the DSVA, the DP simply closes valve 18 and pulls the DSVA out of valve 50, as indicated in FIG. 10B. When extension 20 is pulled away from ball 50B, spring 50S will force ball 50B back to its closed position shown, where it will close off hosel 50L and 14. Thus even though the DP removes the DSVA from valve 50, no vacuum sound will be heard since the hose 14 will automatically be closed by valve 50 when the DSVA is removed.

Hose valve 50 can be operated with one hand by providing a lower body portion on hosel 50L, similar to lower body 24O (FIG. 8A). Then the hose and its valve can be stored in an instrument holder similar to holder 24R (FIG. 8) on the chairside stand. Then the DSVA and the attached hose and valve can be removed for use, replaced, or the DSVA can be separated from the hose and valve, all with one hand without having to touch the hose or its valve.

Description And Operation—FIGS. 11–12C—Drill Assembly

As indicated supra, the problems of inadequate asepsis of the vacuum ejectors of FIG. 1 are also present with drill 100 of FIG. 11 since the DP's hands can touch connector nut 108 and air/water (two-lumen) supply hose 106.

To remedy this problem, we provide a flange guard 110 (FIGS. 12 and 12A) between the nut and the drill's body 102, on the distal side of the drill's washer 112. Flange guard 110 preferably is made of HDPE and has an outer diameter of 32 mm. It is thin enough (about 2 mm) to be retrofitted to an existing drill assembly. To install it, an existing drill assembly is disassembled as shown in FIG. 11, flange guard 110 is positioned on the proximal end of drill body 102, over its screw threads ridges 114, washer 112 is similarly installed, and nut 108 with hose 106 attached is reassembled by screwing the nut over the ridges in the usual manner.

The resultant assembly (FIG. 12A) thus includes protective flange 110 at the proximal end of the drill assembly for preventing the DP's hands from touching and contaminating non-sterilizable nut 108 or hose 106 and for providing all of the other advantages of the assembly of FIG. 2.

To provide an even greater degree of protection, a handle extension, analogous to extension 20 of FIGS. 2A and 2B, can also be retrofited to the drill. Such an extension is shown in the exploded view of FIG. 12B and comprises an outer sleeve 116 and an inner conduit body 118 for carrying the air and water from hose 106. Body 118 is assembled within outer sleeve 116 and the female or distal end of sleeve 116 is assembled to body 102. Then flange 110 is assembled to screw threads 120 on the proximal end of sleeve 116 and nut 108 with washer 112 is assembled in the usual manner. The handle extension provides a greater holding area for the DP and thus even further minimizes the chance of touching and contaminating nut 108 or hose 106, similar to the manner in which handle extension 20 of FIGS. 2A and 2B operates.

As an even further protective feature, a locking foot 122 (FIG. 12C) can be incorporated on nut 108 so that the drill can be separated from the nut with one hand by using the instrument holder of the chairside stand as another hand. This is analogous in structure and operation to footed leg 24Q of FIG. 8A. In addition, the assembly of FIG. 12C is shown with a newer type quick disconnect 124 where the male part is on the nut and the female part is on the drill's body. 102A. Foot 122 may be about 5 mm wide and about 10 mm long.

Description And Operation—FIGS. 13–15—Air/Water Valve

As also indicated supra, the problems of inadequate asepsis of the vacuum ejectors of FIG. 1 and the drill of FIG. 11 are also present with air/water valves (AWVs) of the type shown in prior-art FIG. 13. The valve of FIG. 13 comprises a single nozzle 202 and a pair of operating buttons for causing either air or water to be emitted in a stream (not shown) from nozzle 202. Only one button 204 is shown; the other button is behind button 204. The valve also includes a handle 212 and a hose valve body 208 into which a hose valve (not shown) is included. A junction 210 is positioned between valve body 208 and handle 212 for allowing the handle to be removed from valve body 208 so that the handle can be sterilized and replaced. A two-part supply hose 206 has two parts which supply air and water under pressure to the valve.

When the valve of FIG. 13 is used by DPs, the DP's hands will touch and contaminate valve body 208, junction 210, and hose 206 in the manner aforedescribed, thereby leading to cross-contamination of patients and unwanted transmission of MOs.

In accordance with the invention, we provide a handle extension 214 and a flange guard 216 between handle 212 and valve body 208. This handle extension and flange guard force and allow the DP to hold the air-water valve only on the distal side of the flange guard so that the DP's contaminated hands never touch or handle body 208 or hose 206, in the manner aforedescribed.

As shown in FIG. 14A, flange guard 216 comprises a separate washer or annular member, similar to those of FIGS. 2 et seq., but without the tapering inner part. Extension 214 comprises a tubular sleeve having a male thread on its narrowed proximal end and a female thread at its distal end. The male thread slips through the opening of flange guard 216 with a close fit so that flange guard 216 fits snugly against the shoulder formed by the narrowed proximal end. The male threads mate with female threads (not shown) in the distal end of body 208. An insert 218 comprising a cylindrical body having two lumens or tubes therethrough for air and water fits into the sleeve and connects the air and water tubes in valve body 208 to those in handle 212, respectively. The distal end of the sleeve is threaded with female threads which mate with male threads (not shown) on the proximal end of handle 212.

In lieu of two separate parts, handle 214 and flange guard 216 can be formed as one integral part, as shown at 220 in FIG. 15.

Description And Operation—FIGS. 16A-E—Other TCEs

In lieu of the flange guards shown in previous Figures, the DP's hand can be kept away from the hose and proximal end of the instruments with other types of Tactile Circumferential Elements (TCEs) on or attached to the DP's instruments. Several such variations are shown in FIGS. 16 to 16E.

In FIG. 16, the TCE comprises a flange guard 300, but attached to a location spaced in from the ends of a handle extension 302, rather than at one end thereof. As in FIG. 2, the handle extension with the flange guard is inserted into the instrument assembly between the instrument and its hose to prevent the DP from touching the hose or the proximal end of the assembly.

Figure 16A:
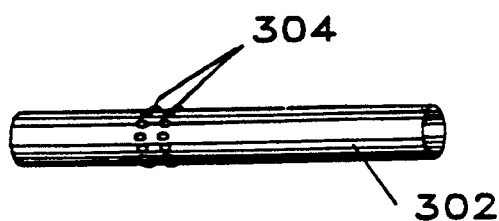

The TCE may comprise a handle extension with a single or plural ring of small nubbins or protrusions 304, as shown in FIG. 16A (two rings of nubbins). Each nubbin may be an integral, rounded, convex protrusion about 1-2 mm high and about 3-4 mm long; the two rings may be about 3-4 mm apart and each nubbin may be about 1 mm from its adjacent nubbins in its ring. While we presently believe that these rings are not as effective as a flange since the DP's hand can slip over the rings, they do take less space and still warn the DP, by tactile sensation, that his or her hand should not cross over the line demarcated by the rings. We prefer two rings since if the DP's hand touches the more distal ring, this will alert the DP not to go any farther, still leaving the proximal ring in a safe area.

Figure 16B:
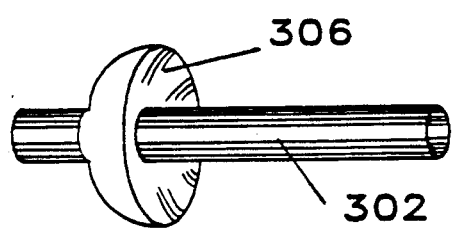

As shown in FIG. 16B, the TCE may be a flange guard having a dome shape, as shown at 306, with the concave side of the dome facing the distal end of the instrument.

Figure 16C:
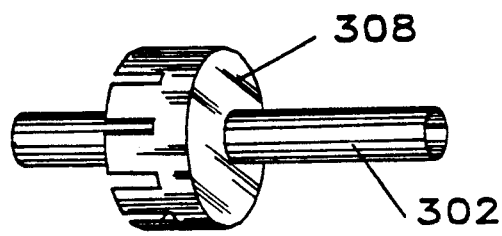

Alternatively, the TCE may be a flange guard with a cylindrical shape with one closed end and the other end having a castellated form, as shown at 308 in FIG. 16C. While the castellated end provides a very tactile sensation to the DP, it may be plain.

Figure 16D:
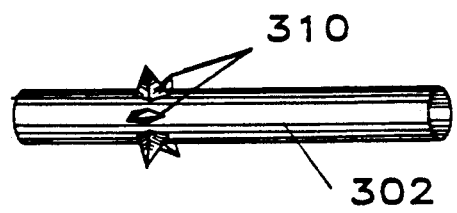
Figure 16E:
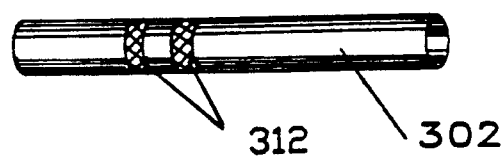

FIG. 16D shows a TCE in the form of a ring of small pyramids 310, each about 3-4 mm high, about 3-4 mm wide at their base, and about 2 mm apart. These provide a highly tactile sensation.

The TCE need not be a protrusion, but can merely be a roughened, scored, filigreed, or knurled ring or rings on the handle extension, as shown at 312 in FIG. 16E. These rings will still alert the DP not to cross the line which they demarcate. The knurling can be in the usual criss-cross pattern with lines about 300 microns deep and 800 microns apart.

Description and Operation—FIG. 17—Electronic Sensors

In lieu of a TCE, other means of warning the DP that his or her hand has wandered too far may be employed. As shown in FIG. 17, a ring of conductive contacts 314, each about 2 mm wide and about 10 mm long, may be spaced about 1 mm apart around handle extension 302. Alternate contacts are commonly connected electrically, e.g., by jumpers 316, so as to provide two sets of contacts which are interleaved around the ring. The two sets are connected by two respective leads 318 to an alarm circuit 320 which is arranged to drive a speaker 322 or other annunciator, such as a piezoelectric element. Alarm circuit 320 is arranged to drive the two sets of contacts with an RF (radio frequency) signal. If the DP bridges any adjacent pair of contacts with a hand or finger, the RF signal will travel between the contacts by conduction and capacitance so as to create a current which will be sensed by the alarm circuit. The alarm circuit will thus activate speaker 322 to alert the DP that his or her hand has wandered too far.

Description and Operation—FIG. 18—Automatic Valve

In lieu of a manually operated valve, an automatic hose valve may be employed which turns on the vacuum when the HVE is inserted into the patient's mouth. Such an automatic hose valve will normally be off, but will automatically open to provide a vacuum or suction at the tip of the HVE tube when it is inserted into a patient's mouth. Thereby the DP does not have to touch the valve manually, thus increasing asepsis.

Such a valve is part of a system shown in FIG. 18. It comprises a HVE tube 400, similar to the one in FIG. 1, but with the addition of a ring of contacts 402 similar to contacts 314 of FIG. 17. The tip of tube 400 is beveled as is the tip 10A of FIG. 1 and contacts 402 extend around and up to the beveled edge. As with the contacts of FIG. 17, alternate contacts are commonly connected electrically, e.g., by jumpers (not shown but similar to jumpers 316 of FIG. 17), so as to provide two sets of contacts which are interleaved around the ring. The two sets are connected to a control circuit 404 by two contacts 406 which are embedded in tube 400. Circuit 404 is arranged to supply a potential difference across conductors 406 and is highly sensitive to any current flow in conductors 406. Thus if any adjacent pair of contacts in ring 402 are bridged electrically, e.g., by saliva in the patient's mouth, or by simple resistance of the oral mucus membrane, circuit 404 will sense this current and provide a suitable output signal. This output signal will cause a solenoid-operated valve 408 to turn on. Valve 408 preferably is connected in the path of hose 14 in the chairside dental stand (not shown) so that when it turns on, the vacuum supplied to the proximal end of hose 14 will be communicated to tube 400 to provide suction at its tip.

Control circuit 404 may comprise a sensitive bridge circuit with an operational amplifier output. Circuit 404 is connected electrically to valve 408, preferably by an RF link. Alternatively, wires may be run through hose 14 from circuit 404 to valve 408. Circuit 404 contains a suitable energy cell, but valve 408 preferably is connected to the mains supply since it is in the dental stand.

Control circuit 404 includes its own housing into which tube 400 is held by friction fit. The housing preferably contains a foot 122 identical to that of FIG. 12C so that tube 400 may be removed with one hand without touching the housing of circuit 404. Of course tube 400 includes a flange guard 22 to prevent the DP's hand from touching the housing of control circuit 404.

Since the system of FIG. 18 will be self-starting when tube 400 is inserted into a patient's mouth, the DP need not touch any valves and thus the risk of cross-contamination is substantially reduced. When tube 400 is removed from the patient's mouth, the vacuum will terminate since no membrane or saliva will bridge the contacts in ring 402. As with the drill of FIG. 12C, the instrument (tube 400) can be removed from the housing of the control circuit with one hand by virtue of lock foot 122.

In lieu of use with a vacuum-supplied instrument, the automatic valve arrangement may be used with any instrument which (a) is to be inserted into a body cavity, or (b) placed adjacent body tissue, and which is to be supplied with fluid, or even electrically operated, when contact with tissue or fluid is made.

Summary, Ramifications, and Scope

The reader will thus see that we have provided various aseptic dental valves and instruments which prevent MOs from travelling between patient's mouths, thereby reducing the spread of infectious diseases, including AIDS, which prevent MOs from cross-contaminating patients via instruments, their holders, and/or the hands of DPs, which avoid the need to chemically or thermally sterilize dental hoses, which prevent such cross-contamination via dental ejectors, drills, valves, air-water valves or syringes, etc., which provide a viable alternative to all non-sterilizable instrument holders, which provide a dental surgical suction tip which will not return to a straight shape after it is bent to a desired shape, which save time, annoyance, and distraction during operative procedures, which prevent the rushing sound which occurs when a suction tube and valve are removed from a vacuum hose, which avoid the need to turn off the vacuum at its source or the hose valve during this operation, which avoid the need to turn on the valve or source again after a new valve is installed, which avoid any delay associated with the re-turn-on of the source, which provide dental suction tubes and instruments which can be disassembled with one hand and without the use of two hands, thereby to further reduce soiling of valves, vacuum hoses, and instrument holders with MOs from the patient's mouth, which prevent particles which are sucked from the patient's mouth from lodging in the valve and to prevent good particles from lodging in the sediment collector, which avoid the need to disassemble the valve due to particles lodging therein, which avoid the need to remove particles from the vacuum hose or the sediment collector, which avoid the need to sterilize good pieces which have been recovered from a sediment collector or hose, which prevent the above-noted cross-contamination in non-dental areas, which provide a flange or tactile circumferential element for dental instruments which prevent or warns DP not to touch certain components, which provide visual, tactile, and audible warning mechanisms for this purpose, and which provide automatically starting vacuum hoses or electrically operated instruments so that the DP need not touch any valves.

While the foregoing drawings and specification contain many specificities, these should not be considered as limitations on the invention since many variations are possible within its scope. For example the instruments can be made of other materials than as shown, their shape can be changed, the size, shape, and position of the TCE can be changed, etc. The components of the invention are not limited to dental instruments, but can be used for cosmetic and other medical instruments.

Accordingly the full scope of the invention should be determined by the appended claims and their legal equivalents, and not by the examples given.

We claim:

1. A dental instrument for preventing a user of said instrument from touching a supply line for said instrument, thereby to reduce the transmission of microorganisms via contamination of said supply line:

said dental instrument having distal and proximal ends, said dental instrument having a working tip at said distal end, said working tip being arranged to perform a predetermined function in the oral cavity of a patient, said proximal end of said dental instrument including line connection means for connecting said instrument to said supply line arranged to convey a fluid to or from said instrument, said dental instrument having an elongated, hand-graspable handle extension adjacent and proximal to said tip, said handle extension being at least about 100 millimeters long so that said handle extension, and hence said dental instrument, can be held by an adult human hand without having to touch said line connection means, said elongated, hand-graspable handle extension including aseptic guard means for preventing said user of said instrument from touching said supply line for said instrument, said aseptic guard means comprising indicating means arranged to provide a palpable indication to said user of said instrument if said user attempts to move his or her hand past said indicating means toward said supply line, said indicating means being mounted at said proximal end of said elongated hand-graspable handle extension and adjacent said line connection means, said indicating means comprising a member which protrudes out from said elongated handle extension at least about 10 millimeters, whereby said indicating means will prevent a user of said instrument from moving his or her hand past said hand-graspable handle extension toward said line connection means, so that said user's hand will not touch or contaminate said supply line or any other difficult-to-sterilize parts connected to said instrument.

2. The dental instrument of claim 1 wherein said indicating means comprises a flange guard surrounding said instrument and protruding therefrom.

3. The dental instrument of claim 2 wherein said flange guard comprises a circular disc.

4. The dental instrument of claim 3 wherein said circular disc has a center hole which is fitted over and held to said instrument by friction fit.

5. The dental instrument of claim 3 wherein said circular disc has an annular shape with a center hole with side surfaces which taper out to said center hole for stabilizing said disc on said instrument.

6. The dental instrument of claim 3 wherein said circular disc has opposing major surfaces with concave and convex shapes.

7. The dental instrument of claim 3 wherein said circular disc has a skirt with a castellated edge.

8. The dental instrument of claim 1 wherein said indicating means comprises a circumferential band.

9. The dental instrument of claim 1 wherein said elongated handle extension is circular in shape and is about 127 millimeters long.

10. The dental instrument of claim 1, further including a manually operated valve mounted between said elongated handle extension and said working tip.

11. The dental instrument of claim 10 wherein said manually operated valve includes a debris-catching screen therein.

12. The dental instrument of claim 1, further including line valve means, and further including a supply line connected to a proximal end of said instrument via said line valve means, said line valve means being arranged to close said supply line in response to removal of said instrument from said line valve means.

13. The dental instrument of claim 12 wherein
said line valve means comprises a housing having an axial hole therethrough and
an obturator body pivotably mounted in said housing and also having an axial hole therethrough and an obturating area at one end thereof,
said obturator body being mounted and shaped such that when it is (a) pivoted to one position in said housing, its through hole will be aligned with said axial hole in said housing and (b) pivoted to another position in said body, said obturating area will occlude said hole in said housing such that said line valve means will be closed,
whereby a user of said instrument can close said line valve means when removing said instrument by tilting said instrument to move said obturator body to said other position.

14. The dental instrument of claim 12 wherein said line valve means comprises a housing having an axial bore therethrough and an obturator seat defining one part of said bore, and an obturator translatably mounted in said housing and urged to an obturating position on said seat by a spring, but positioned to be cammed away from said seat when a male connector is inserted into said bore of said housing, whereby said line valve means will automatically close when said male connector is removed from said housing and will automatically open when said male connector is inserted into said housing.

15. The dental instrument of claim 14 wherein said housing comprises an obturator-guiding bore extending at an acute angle to said axial bore and communicating with said axial bore, said obtruator comprising a ball and spring, said ball and said spring being positioned in said obturator-guiding bore so that said spring constantly urges said ball toward said axial bore.

16. The dental instrument of claim 12 wherein said line valve means comprises a housing having a shoulder facing said line, such that when said line valve means is inserted into an instrument holder having an upwardly facing shoulder, it will be restrained from falling through said instrument holder, said housing also having a foot comprising a rigid member projecting from a side of said housing, whereby when said member is positioned under a portion of said instrument holder, said housing will be locked in said instrument holder against any upward force thereon, whereby said instrument can be pulled out of said line valve means with an upward pull using a single hand.

17. The dental instrument of claim 16 wherein said foot is attached to said housing via a leg extending from a proximal side of said housing, said member extending from a distal end of said leg.

18. A dental instrument which includes an aseptic guard for preventing a user of said instrument from touching a supply line for said instrument, thereby to reduce the transmission of microorganisms via contamination of said supply line:
    said dental instrument having distal and proximal ends,
    said distal end having a working tip arranged to perform a predetermined function in the oral cavity of a patient, said proximal end of said dental instrument including line connection means for connecting said dental instrument to a supply line arranged to convey a fluid to or from said instrument,
    said dental instrument having an elongated, hand-graspable handle extension adjacent to and proximal from said tip, said elongated, hand-graspable handle extension being at least about 100 millimeters long so that said elongated, hand-graspable handle extension, and hence said instrument, can be held by an adult human hand without having to touch said line connection means,
    said aseptic guard comprising indicating means mounted at said proximal end of said elongated, hand-graspable handle extension and adjacent to said line connection means,
    said indicating means being arranged to provide an indication to said user of said instrument if said user attempts to move his or her hand past said hand-graspable portion toward said line connection means,
    said indicating means comprising a circumferential band of electrical sensor elements and means for indicating if said hand touches said elements.

19. A method of using a medical instrument of the type which (a) is connected to a fluid supply line, (b) has proximal and distal ends, said proximal end being connected to said fluid supply line by line connection means and said distal end having a working tip portion, (c) has an elongated handle extension adjacent and proximal to said line connection means, said elongated handle extension being at least about 100 millimeters long so that said handle extension can be held by an adult human hand without touching said fluid supply line, said elongated handle extension having a proximal end adjacent said line connection means, and (c) has palpable means at said proximal end of said elongated handle extension and adjacent said line connection means, said method comprising:
    holding said instrument by said elongated handle extension, concurrently using said working tip portion on the body of a patient, and concurrently using said palpable means to (a) prevent a user of said instrument from moving his or her hand past said elongated handle extension toward said line connection means and said supply line, and (b) provide an indication to a user of said medical instrument if said user attempts to move his or her hand past said elongated handle extension toward said line connection means and said supply line, such that said user will be prevented from and warned if said user attempts to move his or her hand past said elongated handle extension toward said fluid supply line,
    whereby said user will be able to use said instrument without touching or contaminating said supply line with microorganisms, so that only said instrument and not said supply line need be sterilized or replaced between patients.

20. The method of claim 19 wherein said with palpable means is provided as a flange guard surrounding said medical instrument and protruding therefrom so as to be able to block said user's hand from moving toward said line connection means while said hand holds said handle extension.

21. The method of claim 19 wherein said flange guard surrounding said instrument is provided as a circular disc.

22. The method of claim 21 wherein said circular disc is provided with a center hole fitted over said medical instrument by friction fit.

23. The method of claim 22 wherein circular disc is provided with an annular shape with a center hole with side surfaces which taper out to said center hole for stabilizing said disc on said instrument.

24. The method of claim 19 wherein said palpable means is provided as a flange guard which protrudes out from said instrument by at least about 10 millimeters.

25. The method of claim 19, further including providing a manually operated valve between said elongated handle extension and said working tip.

26. The method of claim 19, further including providing line valve means connecting said supply line to a proximal end of said medical instrument, said line valve means being arranged to close said line in response to removal of said medical instrument from said line valve means.

27. A method for preventing a user of a hand-held medical instrument having a proximal end which includes line connection means for connecting said medical instrument to a supply line and a distal end having a working tip for performing a predetermined function in a patient's oral cavity from touching said supply line, thereby to reduce the transmission of microorganisms via contamination of said supply line, comprising:
    providing said medical instrument with an elongated, hand-graspable handle extension adjacent to and proximal from said working tip, said handle extension being at least about 100 millimeters long so that said handle extension and hence said medical instrument can be held by an adult human hand of a user without touching said fluid supply line,
    providing said medical instrument with indicating means at said proximal end of said elongated handle extension and adjacent to said line connection means, said indicating means being palpable to a user of said medical instrument and being provided so that if said user attempts to move his or her hand past said elongated handle extension toward said line connection means and said supply line, said indicating means will prevent and warn said user from so moving his or her hand, said indicating means comprising a flange guard extending and protruding out from said medical instrument, whereby said user will be able to use said medical instrument to perform a predetermined function in a patient's oral cavity by extending said hand around and gripping said handle extension with said hand, then, while holding said handle extension with said hand, inserting said working tip in said patient's oral cavity, and manipulating said tip in said patient's oral cavity, and using said indicating means to provide an indication to said user of said medical instrument if said user attempts to move his or her hand past said hand-graspable portion toward said line connection means and said supply line.

28. The method of claim 27 wherein said providing said medical instrument with indicating means comprises providing a flange guard having a circular disc.

29. The method of claim 28 wherein said providing a flange guard having a circular disc comprises providing a flange guard having tapered sides.

30. The method of claim 29 wherein said providing a flange guard having a circular disc comprises providing a circular disc having a center hole which is fitted over said medical instrument by friction fit.

31. The method of claim 27, further including providing a manually operated valve between said elongated handle extension and said working tip.

32. The method of claim 27, further including providing line valve means connecting a supply line to a proximal end of said instrument, said line valve means being arranged to close said line in response to removal of said medical instrument from said line valve means.

33. The method of claim 27 wherein said flange guard protrudes out from said instrument by at least about 10 millimeters.

* * * * *